United States Patent
Lin et al.

(10) Patent No.: US 10,238,319 B2
(45) Date of Patent: Mar. 26, 2019

(54) FEATURE POINT IDENTIFICATION METHOD OF MECHANOCARDIOGRAPHY

(71) Applicant: CHANG GUNG UNIVERSITY, Taoyuan (TW)

(72) Inventors: Wen-Yen Lin, Taoyuan (TW); Ming-Yih Lee, Taoyuan (TW); Po-Cheng Chang, Taoyuan (TW); Wen-Zheng Zhou, Taoyuan (TW)

(73) Assignee: Chang Gung University, Taoyuan (TW)

( * ) Notice: Subject to any disclaimer, the term of this patent is extended or adjusted under 35 U.S.C. 154(b) by 0 days.

(21) Appl. No.: 15/716,776

(22) Filed: Sep. 27, 2017

(65) Prior Publication Data

US 2018/0014753 A1 Jan. 18, 2018

Related U.S. Application Data

(62) Division of application No. 14/993,228, filed on Jan. 12, 2016, now Pat. No. 9,833,172.

(30) Foreign Application Priority Data

Feb. 16, 2015 (TW) .............................. 104105227 A

(51) Int. Cl.
| | |
|---|---|
| *A61B 5/0452* | (2006.01) |
| *A61B 5/11* | (2006.01) |
| *A61B 5/0456* | (2006.01) |
| *A61B 5/00* | (2006.01) |

(52) U.S. Cl.
CPC ............ *A61B 5/1102* (2013.01); *A61B 5/0456* (2013.01); *A61B 5/6823* (2013.01); *A61B 5/6824* (2013.01); *A61B 5/6828* (2013.01); *A61B 2562/0219* (2013.01)

(58) Field of Classification Search
CPC ................ A61B 5/1102; A61B 5/0456; A61B 2562/0219
See application file for complete search history.

(56) References Cited

U.S. PATENT DOCUMENTS

| | | | |
|---|---|---|---|
| 2008/0194975 A1* | 8/2008 | MacQuarrie | A61B 5/02 600/483 |
| 2015/0038856 A1* | 2/2015 | Houlton | A61B 5/0402 600/484 |

* cited by examiner

*Primary Examiner* — George R Evanisko
(74) *Attorney, Agent, or Firm* — Rosenberg, Klein & Lee

(57) ABSTRACT

A method to identify feature points associated with the heart valve movement, heart contraction or cardiac hemodynamics is revealed. The mechanocardiography (MCG) is a technology that makes use of vibrational waveforms acquired using at least one gravity sensor attached on one of the four heart valve auscultation sites on the body surface. The data of the electrocardiography (ECG) is recorded simultaneously with the MCG. The feature points are identified by comparing P, R and T points of synchronized ECG with the MCG spectrum. By the time sequences and amplitudes of the feature points, the method provides additional clinical information of cardiac cycle abnormalities for diagnosis.

3 Claims, 30 Drawing Sheets

FEATURE POINT IDENTIFICATION METHOD OF MECHANOCARDIOGRAPHY

REMARKS: CROSS-REFERENCE TO RELATED APPLICATION

This application is a Divisional application of U.S. patent application Ser. No. 14/993,228, filed on 12 Jan. 2016, currently pending, which is based on Taiwan patent application Ser. No. 104105227, filed on 16 Feb. 2015, which are incorporated by reference.

FIELD OF THE INVENTION

The present invention relates to a method of measuring cardiac vibrations on the body surface, especially to identify feature points associated with the mechanocardiography (MCG).

BACKGROUND OF THE INVENTION

Since cardiovascular diseases have accounted for top three of ten causes of death in Taiwan, public awareness on prevention of cardiovascular diseases is increasing. The people with the cardiovascular diseases include older age, hypertension, diabetes, hyperlipidemia, exposure to tobacco, obesity, and a family history of cardiovascular diseases, etc. The doctor diagnose patients by understanding the detail of patient disease history and checking with the equipment such as electrocardiogram (ECG), stress ECG, phonocardiogram, echocardiography, nuclear medical imaging study, cardiac computerized tomography (CT) scan, cardiac magnetic resonance imaging (MRI), etc. There are two major problems of heart valves: valvular stenosis, which is inadequate opening, and valvular regurgitation, which is backward leakage of blood through closed valves. These problems result in elevated pressure or increased volume in heart chambers, leading to deterioration of heart function.

Heart valvular system consists of mitral, tricuspid, aortic and pulmonary valves. Heart valves allow blood to circulate through them when they are open and prevent backward blood flow when they are closed. The mechanisms make unidirectional blood flow possible and preserve energy. Each valve can develop stenotic and regurgitant disorders, and some patients have valvular prolapse of mitral and tricuspide valves, which indicate elongated valves with leaflets prolapsed to the atrial chambers. The circulation of blood in cardiovascular system is as following: deoxygenated blood returns to the right atrium from peripheral venous system via the superior and inferior venae cavae (SVC and IVC). The right ventricle relaxes to allow blood to go into the right ventricle via the tricuspid valve and then contracts to pump blood in the pulmonary circulation via the pulmonary valve. After oxygen ($O_2$) and carbon dioxide ($CO_2$) exchange in the lungs, oxygenated blood returns to the left atrium. The left ventricle relaxes to allow blood to go into the left ventricle via the mitral valve and then contracts to pump blood in the systemic circulation via the aortic valve. During ventricular systole and diastole, forward flow is allowed and backward flow is prevented by functioning valvular opening and closing.

The most commonly available exam of cardiac diseases is ECG, which provides indirect evidences of valvular diseases. For example, aortic stenosis results in ventricular pressure overload and left ventricular hypertrophy. Thus an increased QRS amplitude, ST segment/T-wave abnormalities can be observed in ECG. However, the same findings can be found in other diseases. The evaluation of cardiac systolic and diastolic function requires further chest X-ray, echocardiography and nuclear medical tests. Cardiac murmurs generated by valve insufficiency can be heard using a stethoscope. There are some limitations: a physician being able to check a single auscultation site at a time and the narrow range of human hearing (20 Hz to 20 kHz). Some abnormal heart sounds, such as the third and the fourth heart sounds (S3 and S4) are relatively lower in frequency, which might be beyond the limits of human hearing and are missed in cases. Therefore, phonocardiography is used to record heart sound to check the opening and closing timing of heart valves. There is a time delay between heart valves closing and signal captured on body surface, leading to confusion in clinical evaluation. Chest X-ray reveals calcification of the valves, but it provides limited information of valvular heart diseases and is not a useful tool for continuous monitoring because of radiation. Echocardiography is a useful tool to evaluate cardiac contraction and valvular function. The commonly used echocardiographic modalities include M-mode, 2-D, 3-D, Doppler and contrast echocardiography images. Chamber sizes and valvular motion can be evaluated using M-mode echocardiography, and normal and abnormal blood flow can be detected using Doppler and contrast echocardiography. However, echocardiography machine is bulky, and professional personnel are required, making the exam very inconvenient and not suitable for continuous monitoring.

The conventional ways for checking heart valve defect include ECG, phonocardiogram, echocardiography, and nuclear medical tests. However, these techniques have their limitations while in use. Such as, the ECG can be used to estimate intervals of heart valve operation, but can't be used to check opening and closure of heart valves effectively. The phonocardiograms can be used for checking the opening and closing of heart valves, yet are unable to detect changes in blood flow of the heart. The echocardiography can be used to check the lumen diameter, the heart valve movement, the direction of blood flow, the velocity and turbulence of the blood flow in cardiac vessels, but poses problems in long term monitoring. Thus there is room for improvement and a need to provide a novel method for mechanocardiography that overcomes the shortcomings of conventional ways for checking heart valves. The method not only records heart valve operation and blood flow features for long-term monitoring but also improves convenience and accuracy in measurement.

SUMMARY

Therefore, one of the primary object s of the present invention is to provide a feature point identification method for mechanocardiography that implements mechanocardiography (MCG) and electrocardiography (ECG) simultaneously by measuring vibrations on body surface. The P-wave peak and the R-wave peak of the ECG correspond to the MCG to get two corresponding points. Then a transmitral atrial contraction maximal flow feature point (MFA) between the two corresponding points of the MCG is retrieved. Thus convenience and accuracy of clinical disease assessment are improved.

It is another object of the present invention to provide a feature point identification method for mechanocardiography that retrieves a lateral wall contraction maximal velocity feature point (LCV), a transaortic maximal flow feature point (AF), and a septal wall contraction maximal velocity feature point (SCV) after an R-wave peak corresponding point of the MCG to improve convenience and accuracy of clinical disease assessment.

It is a further object of the present invention to provide a feature point identification method for mechanocardiography that compares the R-wave peak and the T-wave peak of the ECG with the MCG to get two corresponding points. Then a transpulmonary maximal flow feature point (PF) and a lateral wall contraction maximal velocity feature point (LCV) between the two corresponding points are retrieved. Thus convenience and accuracy of clinical disease assessment are both improved.

It is a further object of the present invention to provide a feature point identification method for mechanocardiography that retrieves a transaortic maximal flow feature point (AF), a transpulmonary maximal flow feature point (PF) and a septal wall contraction maximal velocity feature point (SCV) after a lateral wall contraction maximal velocity feature point (LCV) to improve convenience and accuracy of clinical disease assessment.

In order to achieve the above objects, the measurement device of the present invention includes at least one gravity sensor, an electrocardiographic (ECG) sensing module, a processor, a storage unit and a transmission unit. The gravity sensor and the ECG sensing module are electrically coupled to the processor while the processor is electrically coupled to the storage unit and the transmission unit. The storage unit is electrically coupled to the transmission unit.

At least one gravity sensor is placed on at least one of the heart valve auscultation sites correspondingly. The heart valve auscultation sites are on the body surface and correspond to the heart valves. The heart valve auscultation sites include an aortic area, a mitral area, a pulmonary area and a tricuspid area. The ECG sensing module includes three limb leads.

The processor is used to receive at least one MCG obtained by the gravity sensor and the ECG obtained by the ECG sensing module. The processor also retrieves peaks or valleys of P-waves, QRS complexes, and T-waves in the ECG. Then the peaks or valleys of the ECG are compared with at least one MCG to get at least one corresponding point of the MCG. Next a plurality of feature points of the MCG before or after the corresponding point is retrieved. The feature points of the MCG include a transmitral atrial contraction maximal flow feature point (MFA), a lateral wall contraction maximal velocity feature point (LCV), a transaortic maximal flow feature point (AF), a transpulmonary maximal flow feature point (PF), and a septal wall contraction maximal velocity feature point (SCV).

The storage unit receives the feature points of the MCG and records the ECG and the MCG from the processor. The storage unit also delivers the ECG and the MCG to a connected receiving device. The receiving device can be a portable device, a computer, or a display.

A feature point identification method for mechanocardiography of the present invention includes the following steps. Arrange a gravity sensor at an aortic area on the body surface which corresponds to the heart valves to get a first MCG (MCG 1) via the gravity sensor. Then dispose an electrocardiography (ECG) sensing module on a limb lead attachment region on the body surface to get an ECG. Next, retrieve a P-wave peak and an R-wave peak of the ECG and correspond both the P-wave peak and the R-wave peak to the MCG1, respectively, to get a first corresponding point and a second corresponding point. Retrieve a peak with the maximum value between the first corresponding point and the second corresponding point. The peak with the maximum value is a transmitral atrial contraction maximal flow feature point (MFA).

The aortic area is present from the left second intercostal space at the left sternal border, over the sternum rightward, to the right second to third intercostal space at the right sternal border.

The limb lead attachment region includes one right arm (RA), one left arm (LA), and one left leg (LL).

A feature point identification method for mechanocardiography of the present invention includes the following steps. First, place a gravity sensor on an aortic area on the body surface that corresponds to the heart valves to get a first MCG reading (MCG 1) by the gravity sensor. Then arrange an electrocardiography (ECG) sensing module at a limb lead attachment region on the body surface to get an ECG. Next, retrieve an R-wave peak of the ECG and correspond the R-wave peak to the MCG1 to get a second corresponding point. Retrieve a valley with the minimum value and a peak thereafter in turn within an interval of 0.06 second after the second corresponding point. The peak is a lateral wall contraction maximal velocity feature point (LCV).

A feature point identification method for mechanocardiography of the present invention includes the following steps. In the beginning, arrange a gravity sensor at an aortic area on the body surface that corresponds to the heart valves to get a first MCG reading (MCG 1) by the gravity sensor. Then place an electrocardiography (ECG) sensing module on a limb lead attachment region on body surface to get an ECG. Next, retrieve an R-wave peak of the ECG and correlate the R-wave peak to the MCG1 to get a second corresponding point. Retrieve a peak with the maximum value within an interval of 0.07-0.1 seconds after the second corresponding point O2. The peak with the maximum value is a transaortic maximal flow feature point (AF).

A feature point identification method for mechanocardiography of the present invention includes the following steps. First, place a gravity sensor on an aortic area on the body surface that corresponds to the heart valves to get a first MCG reading (MCG1) by the gravity sensor. Then arrange an electrocardiography (ECG) sensing module at a limb lead attachment region on body surface to get an ECG. Next retrieve an R-wave peak of the ECG and correspond the R-wave peak to the MCG1 to get a second corresponding point. Retrieve a valley with the minimum value and a peak thereafter in turn within an interval of 0.06 second after the second corresponding point while the peak is a lateral wall contraction maximal velocity feature point (LCV). Then again retrieve a peak after the feature point LCV; this peak is a transaortic maximal flow feature point (AF).

A feature point identification method for mechanocardiography of the present invention includes the following steps. First arrange a gravity sensor at an aortic area on the body surface that corresponds to the heart valves to get a first MCG reading (MCG1) by the gravity sensor. Then place an electrocardiography (ECG) sensing module on a limb lead attachment region on the body surface to get an ECG. Next retrieve an R-wave peak and a T-wave peak of the ECG1 and correspond the R-wave peak and the T-wave peak to the MCG1 to get a second corresponding point and a third corresponding point. Again, retrieve a peak with the maximum value within an interval between 0.1 seconds after the second corresponding point and the third corresponding point. The peak with the maximum value is a transpulmonary maximal flow feature point (PF).

A feature point identification method for mechanocardiography of the present invention includes the following steps. At first, set a gravity sensor at an aortic area on the body surface that corresponds to the heart valves to get a first MCG reading (MCG1) by the gravity sensor. Dispose an electrocardiography (ECG) sensing module on a limb lead attachment region on the body surface to get an ECG. Then retrieve an R-wave peak and a T-wave peak of the ECG1 and correspond the R-wave peak and the T-wave peak to the MCG1 to get a second corresponding point and a third corresponding point. Next, retrieve a valley with the minimum value and a peak thereafter in turn within an interval of 0.06 seconds after the second corresponding point. The peak is a lateral wall contraction maximal velocity feature point (LCV). Retrieve a peak with the maximum value within an interval between the feature point LCV and the third corresponding point. The peak with the maximum value is a transpulmonary maximal flow feature point (PF).

A feature point identification method for mechanocardiography of the present invention includes the following steps. First, arrange a gravity sensor at a mitral area on the body surface that corresponds to the heart valves to get a second MCG reading (MCG 2) by the gravity sensor. Then place an electrocardiography (ECG) sensing module on a limb lead attachment region on the body surface to get an ECG. Next retrieve a R-wave peak and a T-wave peak of the ECG1 and correspond the R-wave peak and the T-wave peak to the MCG2 to get a fourth corresponding point and a fifth corresponding point. Retrieve a peak with the maximum value in an interval between 0.04 seconds after the fourth corresponding point and the fifth corresponding point while the peak with the maximum value is a lateral wall contraction maximal velocity feature point (LCV).

The mitral area is present from the right fifth intercostal space at the right sternal border to the posterior axillary line.

A feature point identification method for mechanocardiography of the present invention includes the following steps. First, mount a gravity sensor on a pulmonary area on the body surface that corresponds to the heart valves to get a third MCG reading (MCG3) by the gravity sensor. Then dispose an electrocardiography (ECG) sensing module on a limb lead attachment region on the body surface to get an ECG. Next, retrieve an R-wave peak of the ECG1 and correspond the R-wave peak to the MCG3 to get a sixth corresponding point. Retrieve a peak with the maximum value within an interval between 0.07-0.1 seconds after the sixth corresponding point. The peak with the maximum value is a septal wall contraction maximal velocity feature point (SCV).

The pulmonary area is around the second left intercostal space at the left sternal border, up to the first left intercostal space, a lower part of the clavicle, and then down to the third left intercostal space at the left sternal border.

A feature point identification method for mechanocardiography of the present invention includes the following steps. First, arrange a plurality of gravity sensors on an aortic area and a pulmonary area on the body surface that corresponds to the heart valves to get a first MCG reading (MCG1) and a third MCG reading (MCG3), respectively, by the gravity sensors. Then place an electrocardiography (ECG) sensing module on a limb lead attachment region on the body surface to get an ECG. Next, retrieve an R-wave peak of the ECG and correspond the R-wave peak to the MCG1 to get a second corresponding point. Retrieve a valley with the minimum value and a peak thereafter in turn within an interval of 0.06 seconds after the second corresponding point. The peak is a lateral wall contraction maximal velocity feature point (LCV). Then correspond the feature point LCV to the MCG3 to get a seventh corresponding point of the MCG3. At last, retrieve a peak after the seventh corresponding point and this peak is a septal wall contraction maximal velocity feature point (SCV).

A feature point identification method for mechanocardiography of the present invention includes the following steps. First, place a gravity sensor on a tricuspid area on the body surface that corresponds to a heart valve to get a fourth MCG reading (MCG4) by the gravity sensor. Then arrange an electrocardiography (ECG) sensing module on a limb lead attachment region on the body surface to get an ECG. Next, retrieve an R-wave peak and a T-wave peak of the ECG1 and correspond the R-wave peak and the T-wave peak to the MCG4 to get an eighth corresponding point and a ninth corresponding point. Retrieve a peak with the maximum value between the eighth corresponding point and the ninth corresponding point. The peak with the maximum value is a lateral wall contraction maximal velocity feature point (LCV).

The tricuspid area is extended rightward from the left fourth to fifth intercostal space at the right sternal border.

BRIEF DESCRIPTION OF THE DRAWINGS

The structure and the technical means adopted by the present invention to achieve the above and other objects can best be understood by referring to the following detailed description of the preferred embodiments and the accompanying drawings, wherein.

DETAILED DESCRIPTION

Please refer to the following implementations and related details in order to learn about the features and functions of the present invention.

There is a variety of tests available now for checking heart valve problems including ECG, phonocardiogram, echocardiography, and nuclear medical tests. ECG is used to estimate intervals of heart valve operation, but is unable to check the opening and closing of heart valves. Users can check the opening and closing of heart valves via a phonocardiogram, yet are unable to observe changes in the blood flow of the heart. An Echocardiography can be used to check the lumen diameter, the heart valve movement, the direction of the blood flow, the velocity, and the turbulence of the blood flow in the cardiac vessels, but poses problems of convenience and accuracy in measurement. Thus the present invention provides a feature point identification method for mechanocardiography that retrieves vibration signals on body surface as a consequence of cardiac motion by at least one gravity sensor to get an MCG. A variety of peaks and valleys of the MCG are retrieved in turn by comparing the P-wave peak, R-wave peak and T-wave peak of the ECG gotten from the ECG sensing module with the MCG to get feature points related to heart valves, the cardiac cycle, or the blood in the heart. The present invention is a breakthrough method that records heart valve operation or cardiac blood features via portable gravity sensors. The method can be used for long term monitoring with higher convenience and accuracy in measurement.

Figure 1:
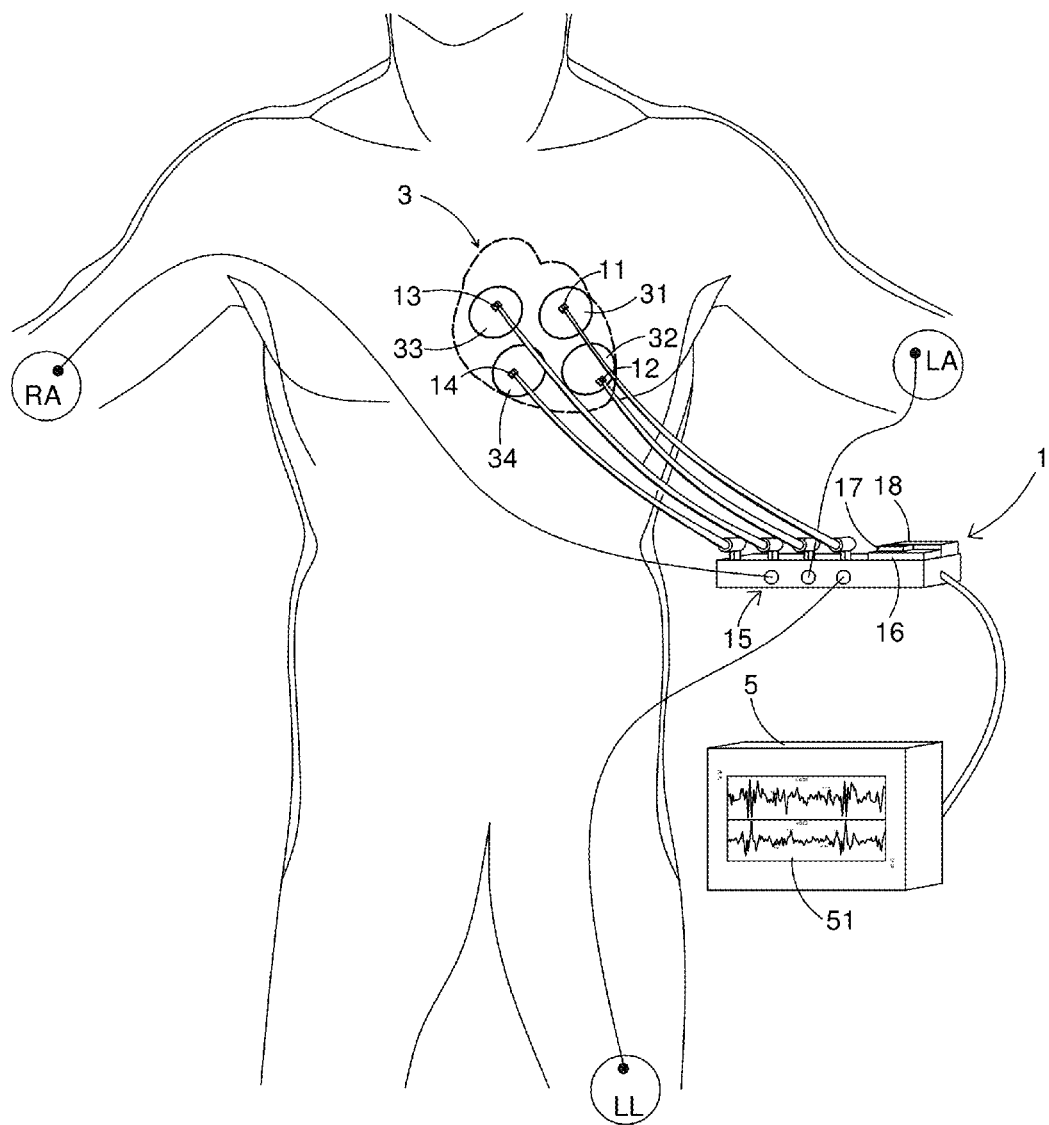
FIG. 1 is a schematic drawing showing the structure of a measurement device that embodies the present invention.
Figure 2:
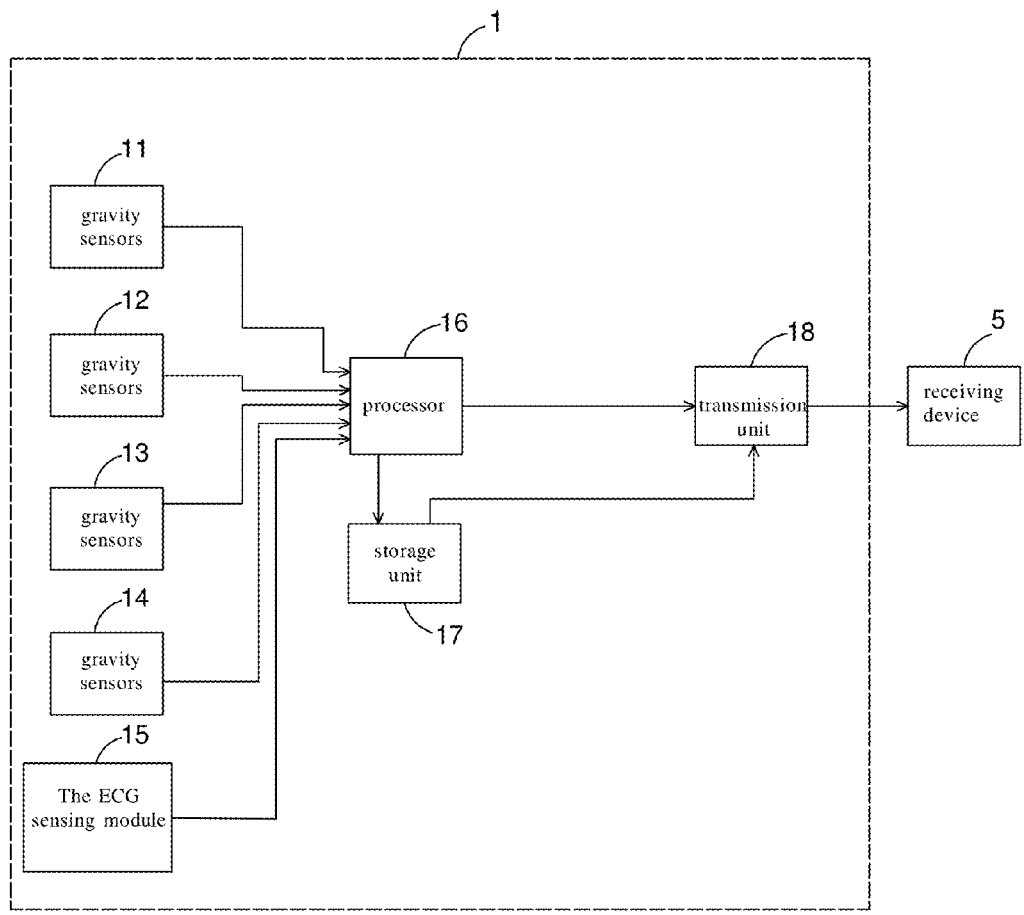
FIG. 2 is a circuit diagram of a measurement device that embodies the present invention.

Refer to FIG. 1 and FIG. 2, a schematic drawing showing the structure and a circuit block diagram of a measurement device of an embodiment according to the present invention, respectively. The hardware of the present invention comprises a measurement device 1 that includes several gravity sensors 11-14, an electrocardiographic (ECG) sensing module 15, a processor 16, a storage unit 17 and a transmission unit 18. The gravity sensors 11-14 and the ECG sensing module 15 are electrically coupled to the processor 16 while the processor 16 is electrically connected to the storage unit 17 and the transmission unit 18. The storage unit 17 is electrically coupled to the transmission unit 18.

Figure 3:
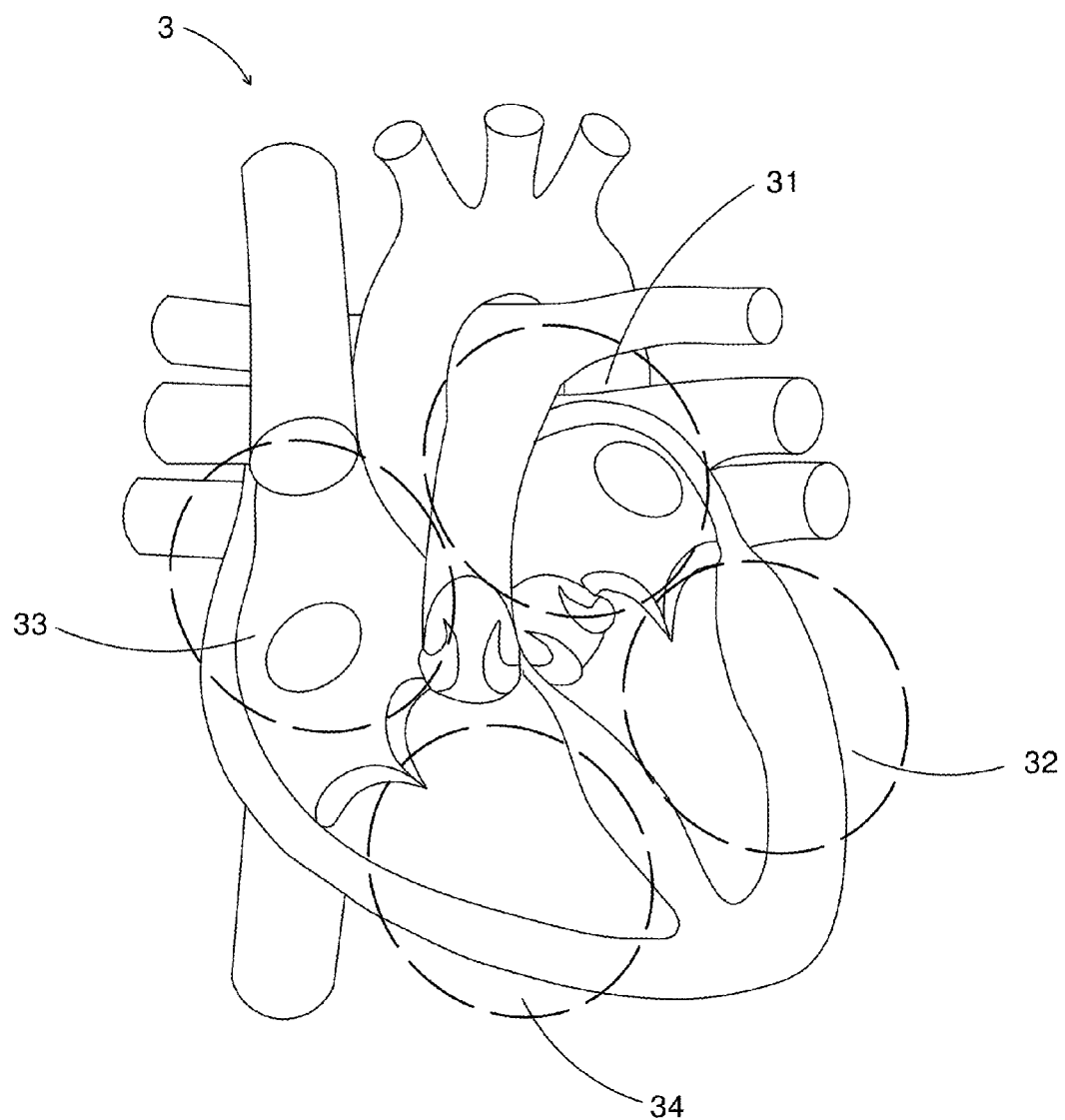
FIG. 3 is a schematic drawing showing heart valve auscultation sites on body surface which pertain to the present invention.

Refer to FIG. 3, at least one of four gravity sensors 11~14 are arranged at the heart valve auscultation sites 3 which are on the body surface and corresponding to the heart valves, including an aortic area 31, a mitral area 32, a pulmonary area 33, and a tricuspid area 34. The aortic area 31 is present from the left second intercostal space at the left sternal border, over the sternum, to the right second to third intercostal space at the right sternal border. The mitral area 32 spans the right fifth intercostal space at the right sternal border to the posterior axillary line. The pulmonary area 33 is around the left 2nd intercostal space at the left sternal border, up to the left first intercostal space, a lower part of the clavicle, and then down to the left third intercostal space at the left sternal border. The tricuspid area 34 extend srightward from the right fourth to fifth intercostal space at the right sternal border. Each gravity sensor 11~14 contains an accelerometer chip. The typical type of accelerometer chip can be piezo-resistive, capacitive, piezoelectric and resonant while the preferred one is produced and sold by the American company ADXL or the European company STM. The accelerometer chip is used to measure the vibrations on the body surface and to acquire at least one mechanocardiography (MCG), which is also known as a seismocardiography (SCG).

The ECG sensing module 15 is disposed on a lead site on the skin area for detecting the electrical activity of the heart on the skin area and producing an electrocardiography. The optimal lead site includes positions for 3 limb leads-one right arm (RA), one left arm (LA), and one left leg (LL) and the lead is preferably attached xproimally to the wrist and the ankle. The positions of the leads shown in FIG. 1 are only an embodiment of the present invention and are not limited to these positions.

The processor 16 is used for receiving at least one MCG and the ECG mentioned above, retrieving peaks or valleys of the P-wave, QRS complex and T-wave in the ECG, and comparing the peaks or valleys of the ECG with the MCG within at least one time interval. Thus a plurality of feature points of the MCG are obtained within the time interval. The optimal processor 16 is a microcontroller unit.

The storage unit 17 used for receiving the feature points of the MCG and recording both the ECG and at least one MCG from the processor 16 can be a Read-Only Memory (ROM), or a Random Access Memory (RAM). If the storage unit 17 is the ROM, it is preferred to access and store signal information through an SD (secure digital) card by which the information is delivered to a receiving device 5 directly. The receiving device 5 can be a portable device, a computer, or a display.

The hardware of the present invention further includes a transmission unit 18 that receives the MCG feature points, the ECG, and at least one MCG from the processor 16, or the MCG feature points and at least one MCG from the storage unit 17. The transmission unit 18 sends the above signal information to the receiving device 5 in a wired or wireless way.

Figure 4:
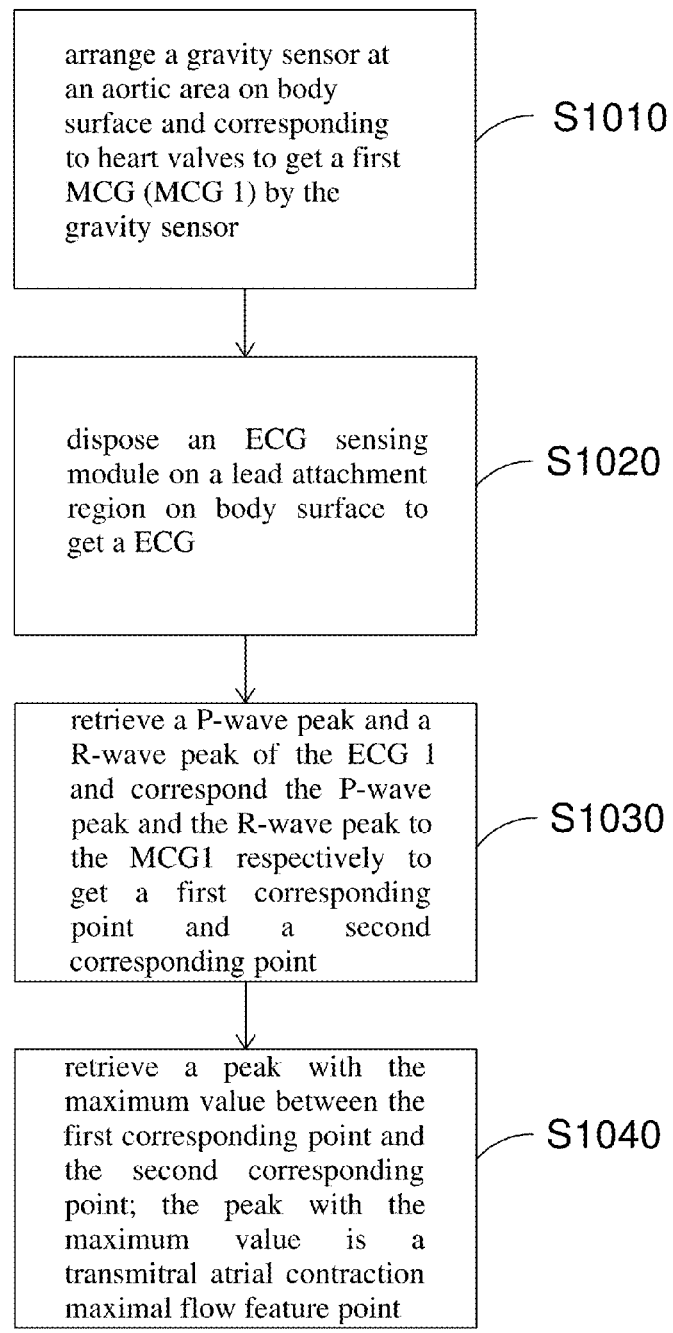
FIG. 4 is the first flow chart showing the steps as related to the present invention.
Figure 5:
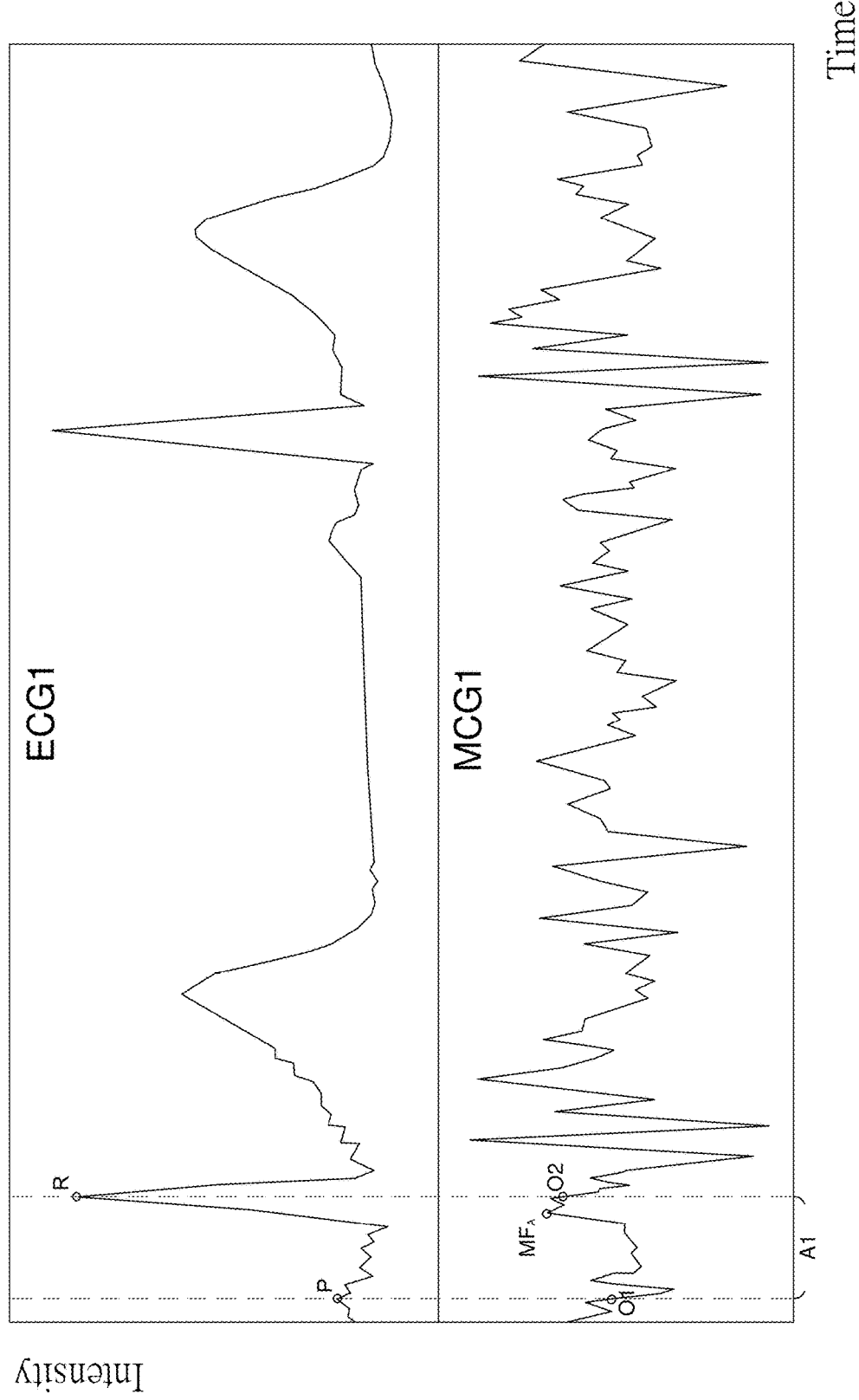
FIG. 5 is the first graph showing signal strength versus time of the first observations according to the present invention.

Refer to FIG. 4 and FIG. 5, a flow chart showing steps and a graph showing signal strength versus time of an embodiment according to the present invention are revealed. The horizontal axis of ECG1 and MCG1 is time (unit: sec) while the vertical axis of ECG1 is signal strength (unit: mV) and the vertical axis of MCG1 is also signal strength (unit: mG). A method of this implementation includes the following steps:

Step S1010: Arrange a gravity sensor at an aortic area on the body surface that corresponds to heart valves to get a first MCG reading (MCG 1) by the gravity sensor;

Step S1020: Place an ECG sensing module on a lead attachment region on the body surface to get an ECG reading;

Step S1030: Retrieve a P-wave peak and an R-wave peak of the ECG 1 and correspond the P-wave peak and the R-wave peak to the MCG1 to get a first corresponding point and a second corresponding point; and Step S1040: Retrieve a peak with the maximum value between the first corresponding point and the second corresponding point. The peak with the maximum value is a transmitral atrial contraction maximal flow feature point.

As shown in FIG. 1 and FIG. 3, in step S1010, the gravity sensor 11 arranged at the aortic area 31 is used for receiving vibrations on the body surface at the aortic area 31 caused by the heartbeat to get the first MCG reading (MCG1).

In step S1020, three limb leads of the ECG sensing module 15 are used for receiving electrophysiological signals of the heart over time to get the ECG1. The processor 16 receives the MCG1 and the ECG1.

In step S1030, the processor 16 retrieves the P-wave peak and the R-wave peak of the ECG 1 and then corresponds the P-wave peak and the R-wave peak to the first MCG1 respectively to get a first corresponding point O1 and a second corresponding point O2 on the MCG1. The horizontal axis (time) of the ECG1 and the horizontal axis (time) of the MCG1 are dependent on each other.

In step S1040, the processor 16 retrieves several peaks and valleys in turn within a time interval A1 between the first corresponding point O1 and the second corresponding point O2 of the MCG1 so as to get the peak with the maximum value. The peak with the maximum value that falls at the position of 0.0225 second before the second corresponding point O2 is a transmitral atrial contraction maximal flow feature point, $MF_A$.

After step S1040, the processor 16 transmits the transmitral atrial contraction maximal flow feature point ($MF_A$), the ECG1 and the MCG1 to the storage unit 17 and the receiving device 5. Thus users can get the information by a display 51 of the receiving device 5 in real time. Moreover, the storage unit 17 not only receives and records the transmitral atrial contraction maximal flow feature point, $MF_A$, the ECG1 and the MCG1, but also transmits the above data to the receiving device 5 when users are not monitoring the data in real time. Thus users can access the data history.

Figure 6:
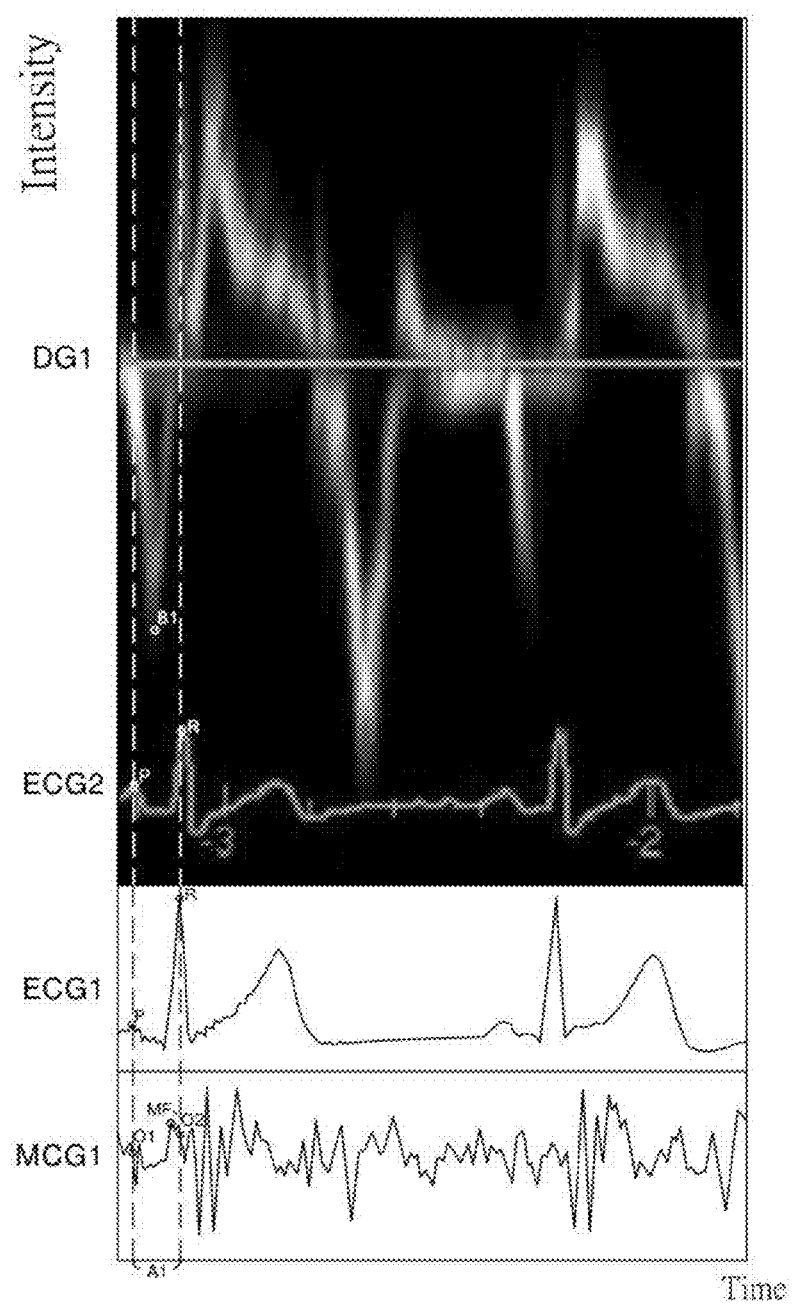
FIG. 6 is the first comparative figure showing signal strength versus time as observed according to the present invention.

Refer to FIG. 6. A comparative diagram shows the signal strength versus time of a first observation. The horizontal axis of ECG1, ECG2, MCG1 and the first Doppler Echocardiography (DG1) is time (unit: sec). The vertical axis of the second ECG (ECG2) is signal strength (unit: mV) and the vertical axis of MCG1 is also signal strength (unit: mG) while the vertical axis of the DG1 is the blood flow rate (unit: cm/s). In this experiment, a Doppler ultrasonic device (not shown in figure) is used to detect heartbeat-induced vibration on the body surface and get the DG1. An ultrasonic transducer of the Doppler ultrasonic device is mounted on a lateral wall of the left ventricle so as to identify the position of the $MF_A$ and of the MCG1 at the same time. The ECG2 is measured simultaneously with the DG1. The ECG1 and the ECG2 are measured at the same time so that the ECG2 and the ECG1 are consistent with each other. Moreover, the DG1, the MCG1, the ECG1 and the ECG2 are also measured at the same time. The limb leads or precordial leads of the ECG2 are placed on the body surface. The six positions for the precordial leads on the chest are as follows: fourth intercostal space at right edge of sternum, fourth intercostal space at the left edge of sternum, midway between the previous two positions, fifth intercostal space at the left midclavicular line, fifth intercostal space at the left anterior axillary line, and fifth intercostal space at the left midaxillary line.

Refer to the DG1. There is a valley B1 with the minimum value showing maximum atrial blood flow or blood pressure and considered to be identical with the feature point $MF_A$ by physicians. Accordance to the valley B1 with the minimum value and the first time interval A1 between the P-wave peak and R-wave peak of the MCG1, it is found that the transmitral atrial contraction maximal flow feature point ($MF_A$) of MCG1 and the valley B1 both fall within the first time interval A1. The feature point $MF_A$ is with the maximum value among the peaks and valleys within the first time interval A1 while the timing of the feature point $MF_A$ of the MCG1 and the timing of the valley B1 of the DG1 are nearly the same. Thus the feature point $MF_A$ of the MCG1 and the valley B1 of the DG1 are identical to each other.

Figure 7:
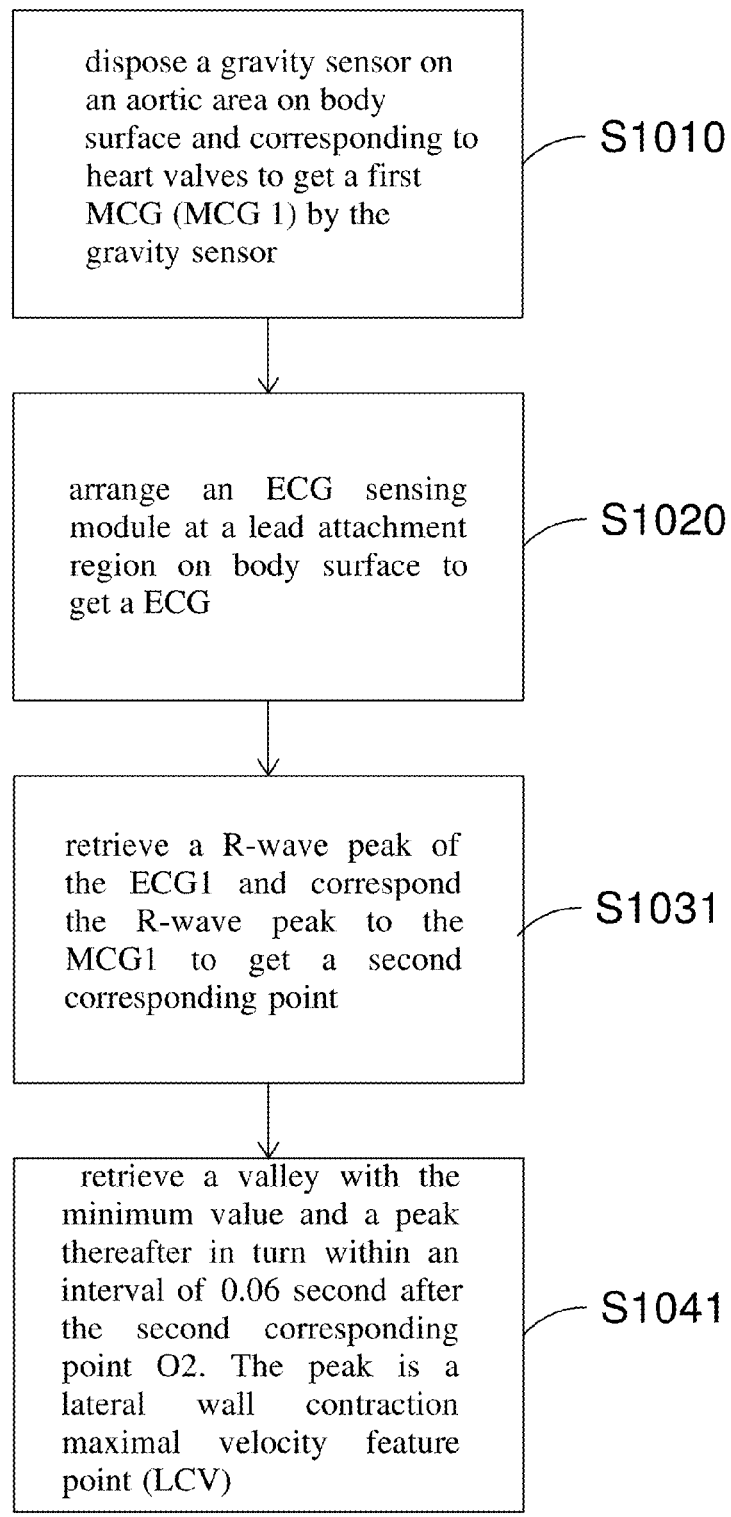
FIG. 7 is the second flow chart showing steps of the second set of observations according to the present invention.
Figure 8:
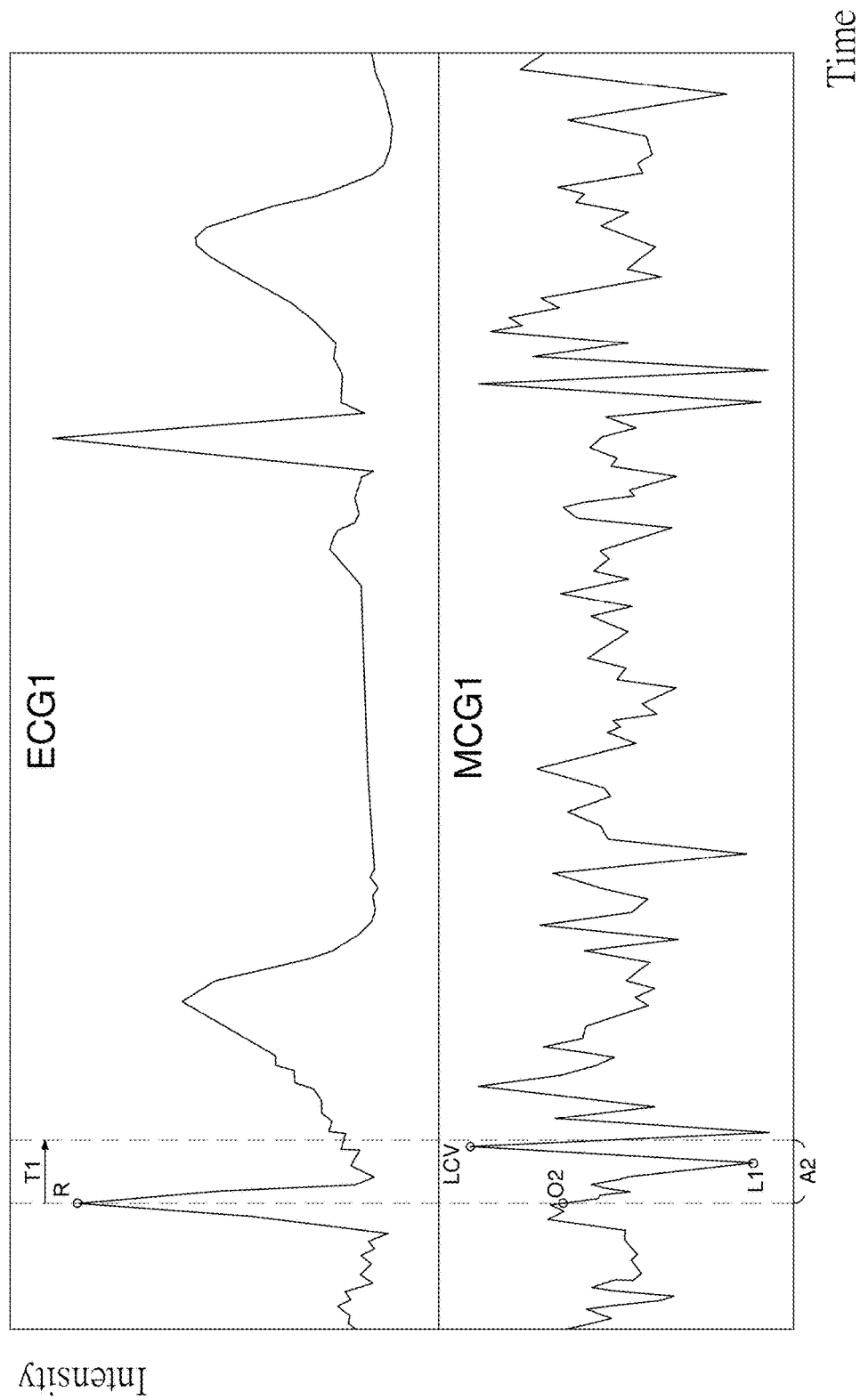
FIG. 8 is the second graph showing signal strength versus time of the second set of observations according to the present invention.

Refer to FIG. 7 and FIG. 8, these figures are flow charts showing steps and a second graph showing signal strength versus time of another experiment, respectively. The unit of the horizontal axis and the unit of the vertical axis of ECG1 and MCG 1 in the second graph showing signal strength versus time of this embodiment are the same, as are those in the first graph showing signal strength versus time of the above experiment. The hardware of this experiment is also the same as the previous experiment. The difference between this experiment and the above experiment is only in the retrieving time so that another feature point is identified. The method to identify this feature point includes the following steps:

Step S1010: Place a gravity sensor on an aortic area on the body surface that corresponds to heart valves to get a first MCG reading (MCG 1) by the gravity sensor;

Step S1020: Arrange an ECG sensing module at a lead attachment region on the body surface to get an ECG;

Step S1031: Retrieve a R-wave peak of the ECG1 and correspond the R-wave peak to the MCG1 to get a second corresponding point; and Step S1041: Retrieve a valley with the minimum value and a peak thereafter in turn within an interval of 0.06 seconds after the second corresponding point O2. The peak is a lateral wall contraction maximal velocity feature point (LCV).

Refer to FIG. 4. Step S1010 and step S1020 are the same as those of the first experiment.

Back to FIG. 1, in the step S1041, the processor 16 retrieves a series of peaks and valleys within a second time interval A2 between the second corresponding point O2 and a first time point T1 after the second corresponding point O2 of the MCG 1 to get the valley with minimum value L1 and the following peak. The peak is preferred to be at the position of 0.0575 seconds after the second corresponding point O2 and is representing a lateral wall contraction maximal velocity feature point (LCV) while the optimal first time point T1 is 0.06 seconds.

After step S1041, the signals are recorded and stored as mentioned in the above experiment.

Figure 9:
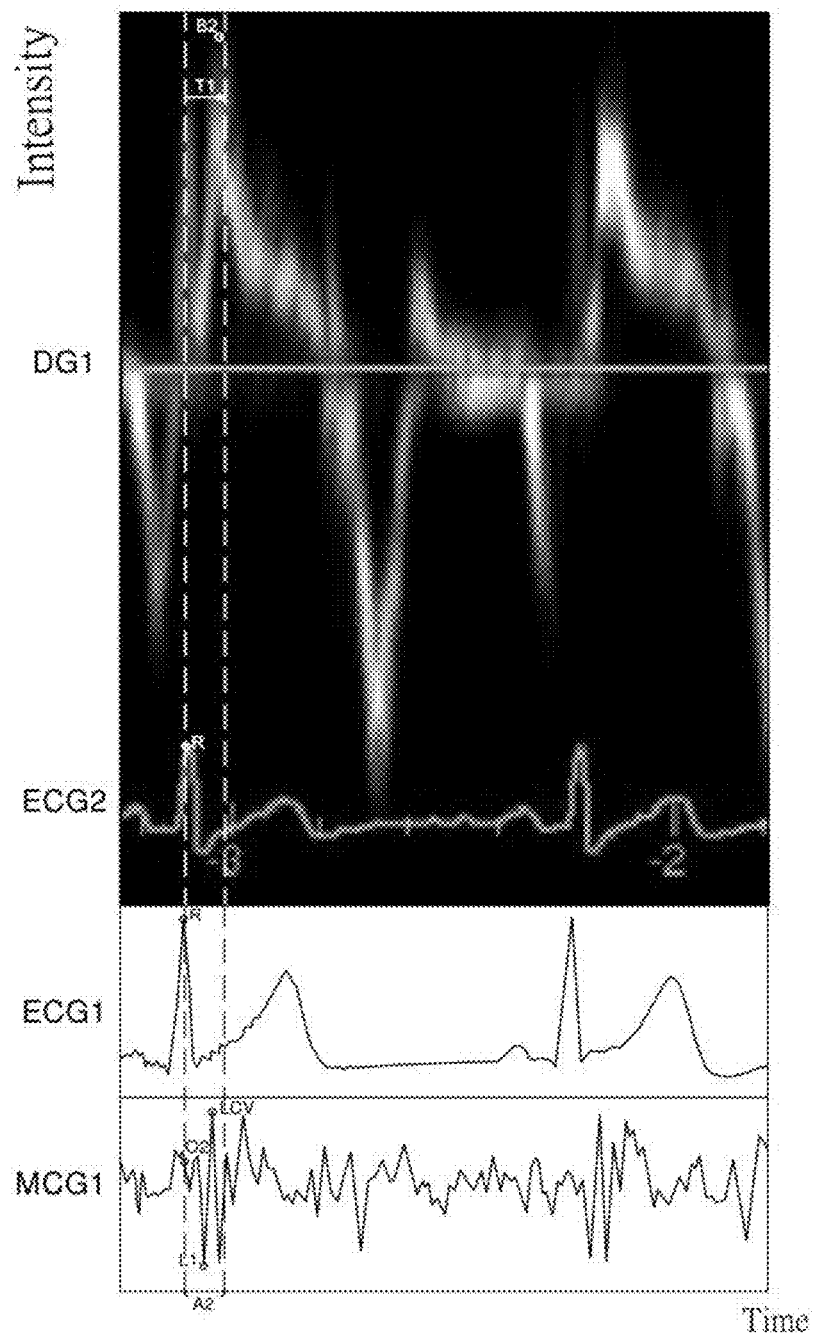
FIG. 9 is the second comparative figure showing signal strength versus time of the second set of observations according to the present invention.

Refer to FIG. 9. This figure is a comparative diagram of a second experiment. The unit of the horizontal axis and the unit of the vertical axis of ECG1, ECG2, MCG1 and DG1 of this experiment is time with respect to those in the comparative diagram showing signal strength versus time of the first embodiment shown in FIG. 6. Similar to the first experiment, this experiment also uses a Doppler ultrasonic device to get the DG1 for identification of the position of the feature point LCV of the MCG1.

Refer to the DG1, a peak B2 with the maximum value that shows the maximum atrial blood flow or blood pressure is considered to be identical with the feature point LCV by physicians. According to the peak B2 with the maximum value and a plurality of peaks and valleys in the second time interval A2 of the MCG1, it is found that both the feature point LCV of the MCG1 and the peak B2 with the maximum value of the DG1 fall in the second time interval A2 after the valley L1 with the minimum value. Thus the feature point LCV of the MCG1 and the peak B2 with the maximum value of the DG1 are identical to each other.

Figure 10:
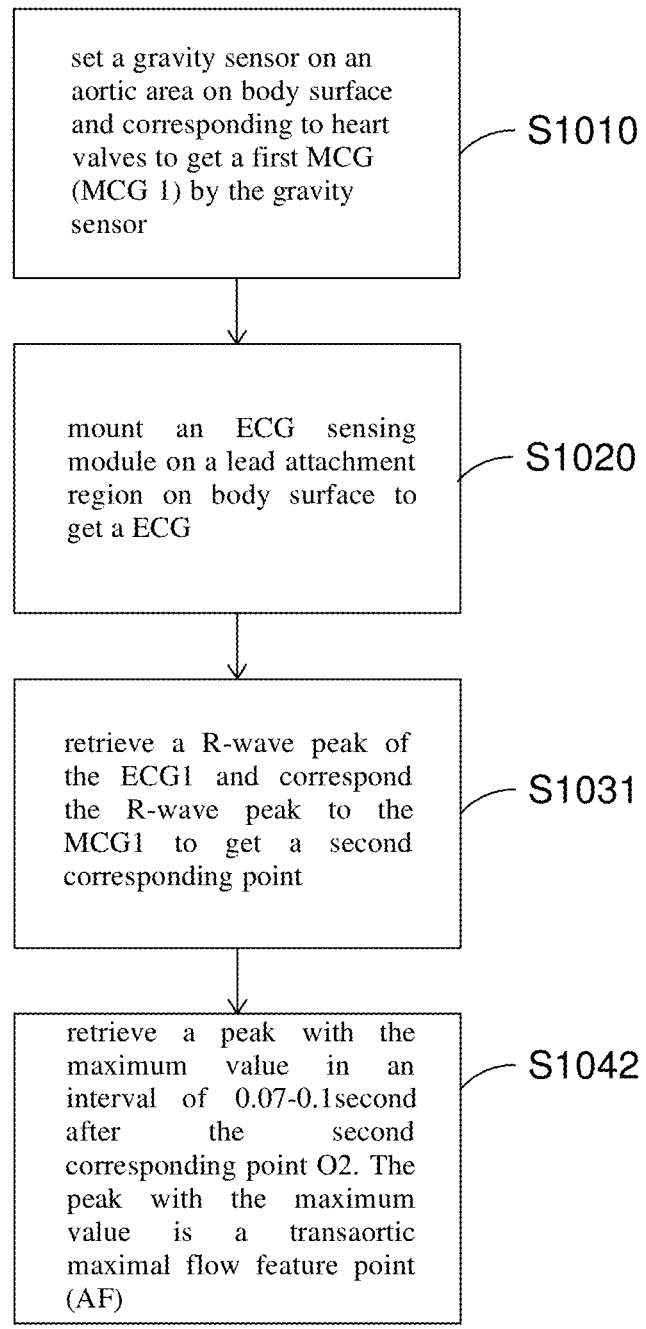
FIG. 10 is the third flow chart showing steps of the third set of observations according to the present invention.
Figure 11:
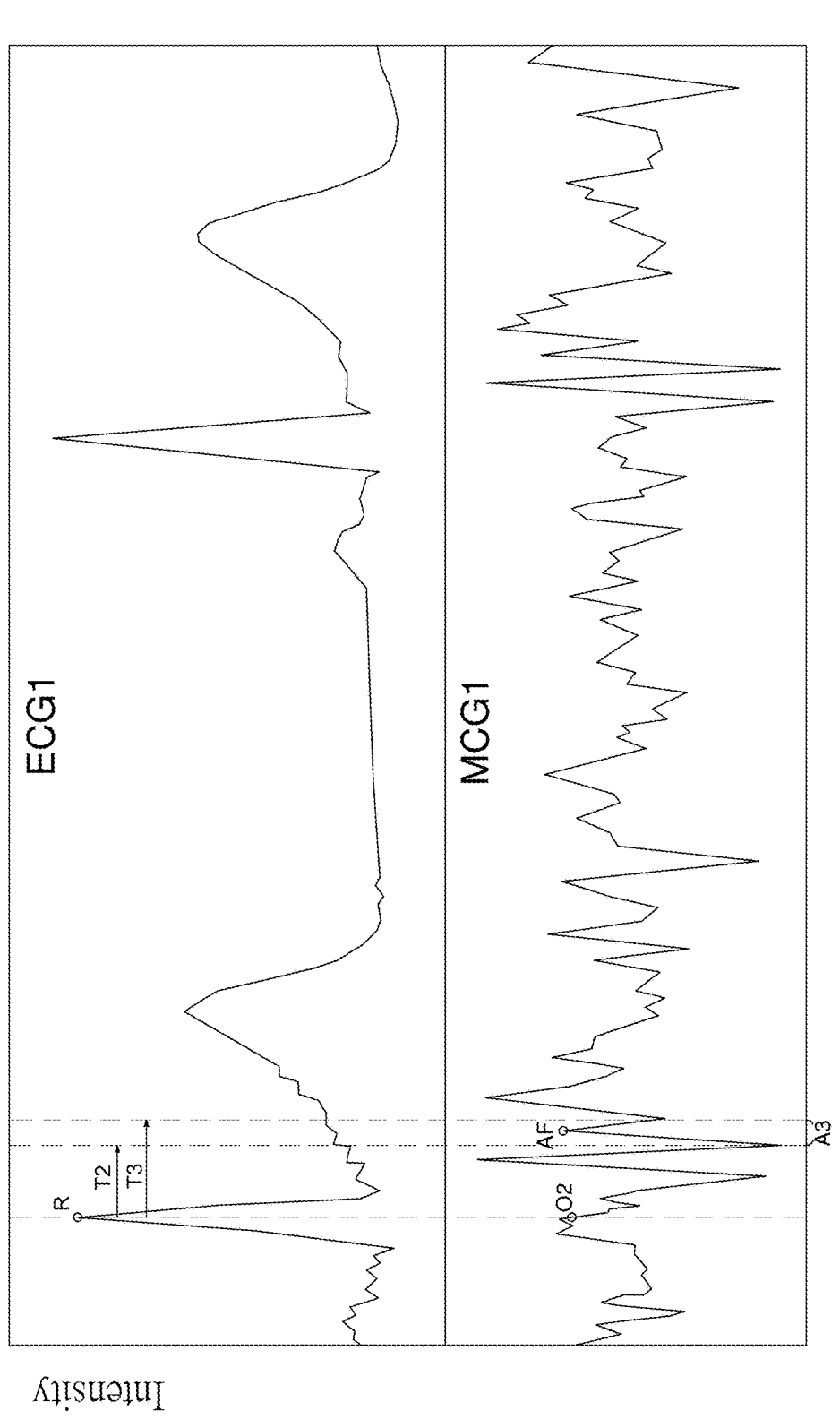
FIG. 11 is the third graph showing signal strength versus time of the third set of observations according to the present invention.

Refer to FIG. 10 and FIG. 11. A flow chart showing steps and a third graph showing signal strength versus time of a further experiment, respectively, are disclosed. The unit of the horizontal axis and the unit of the vertical axis of ECG1 and MCG 1 in the third graph showing signal strength versus time of this experiment are the same as those in the first graph showing signal strength versus time of the first experiment. The hardware of this experiment is also the same with the first experiment. The difference between this experiment and the first experiment is only in the retrieving time so that a further feature point is identified. A method of this experiment includes following steps:

Step S1010: Set a gravity sensor on an aortic area on the body surface that corresponds to heart valves to get a first MCG reading (MCG 1) by the gravity sensor;

Step S1020: Mount an ECG sensing module on a lead attachment region on the body surface to get an ECG;

Step S1031: Retrieve a R-wave peak of the ECG1 and correspond the R-wave peak to the MCG1 to get a second corresponding point; and Step S1042: Retrieve a peak with the maximum value in an interval of 0.07-0.1 seconds after the second corresponding point O2. The peak with the maximum value is a transaortic maximal flow feature point (AF).

Refer to FIG. 4. Step S1010 and step S1020 are the same as those of the first experiment.

Back to FIG. 1, in step S1042, the processor 16 retrieves several peaks and valleys within a third time interval A3 between a second time point T2 and a third time point T3 after the second corresponding point O2 of the MCG 1 to get a peak with the maximum value. The peak with the maximum value is preferred to be at the position of 0.09 seconds after the first corresponding point O1. The peak with the maximum value is a transaortic maximal flow feature point (AF) while the optimal second time point T2 is 0.07 seconds and the optimal third time point T3 is 0.1 seconds.

After step S1042, the signals are recorded and stored as mentioned in the above explanation.

Figure 12:
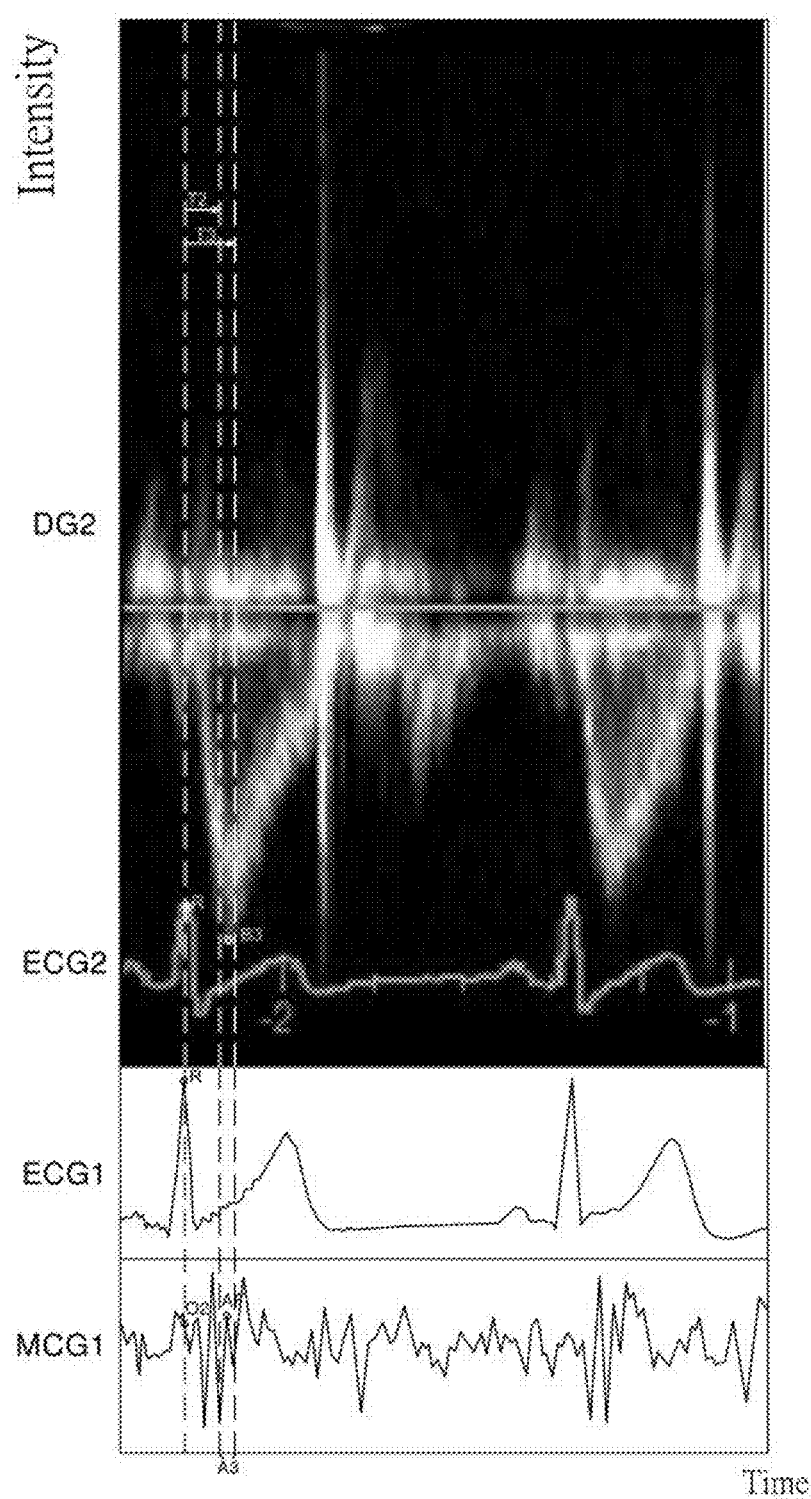
FIG. 12 is the third comparative figure showing signal strength versus time of the third set of observations according to the present invention.

Refer to FIG. 12. This figure is the third comparative diagram showing signal strength versus time of a third experiment. The unit of the horizontal axis and the unit of the vertical axis of ECG1, ECG2, MCG1 and a second Doppler Echocardiography (DG2) are the same as those of the first comparative graph of the first experiment. In this experiment, a Doppler ultrasonic device is used to detect heartbeat-induced vibrations on the body surface and to get the DG2 reading while the DG2, MCG1, ECG1 and ECG2 are measured at the same time. An ultrasonic transducer of the Doppler ultrasonic device is mounted on the left ventricle area and toward the mitral valve so as to get the DG2 for synchronous identification of the position of the feature point AF of the MCG1.

Refer to the DG2. There is a valley B3 with the minimum value showing maximum atrial blood flow or blood pressure at the inner side of left ventricle, which is considered to be identical with the feature point AF by physicians according to the valley B3 with the minimum value and several peaks and valleys in the third time interval A3 of the MCG1. In this experiment, the feature point AF with the maximum value of MCG1 and the valley B3 are falling into the third time interval A3 and are representing the peak with the maximum value and the point with the minimum value among the peaks and valleys within the third time interval A3 respectively. Thus the feature point AF of the first MCG1 and the valley B3 with the minimum value of the DG2 are identical to each other.

Figure 13:
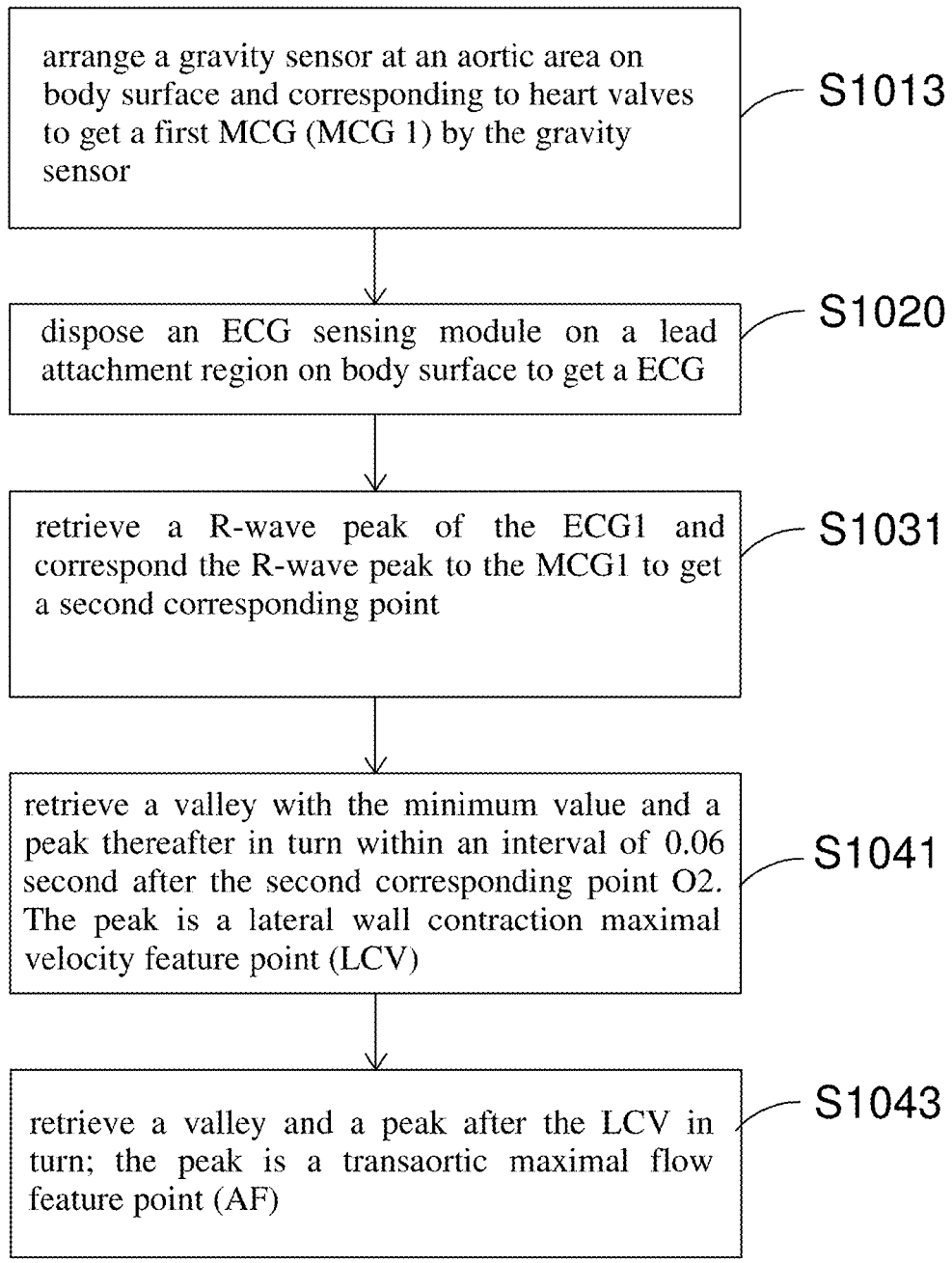
FIG. 13 is the fourth flow chart showing steps of the fourth set of observations according to the present invention.
Figure 14:
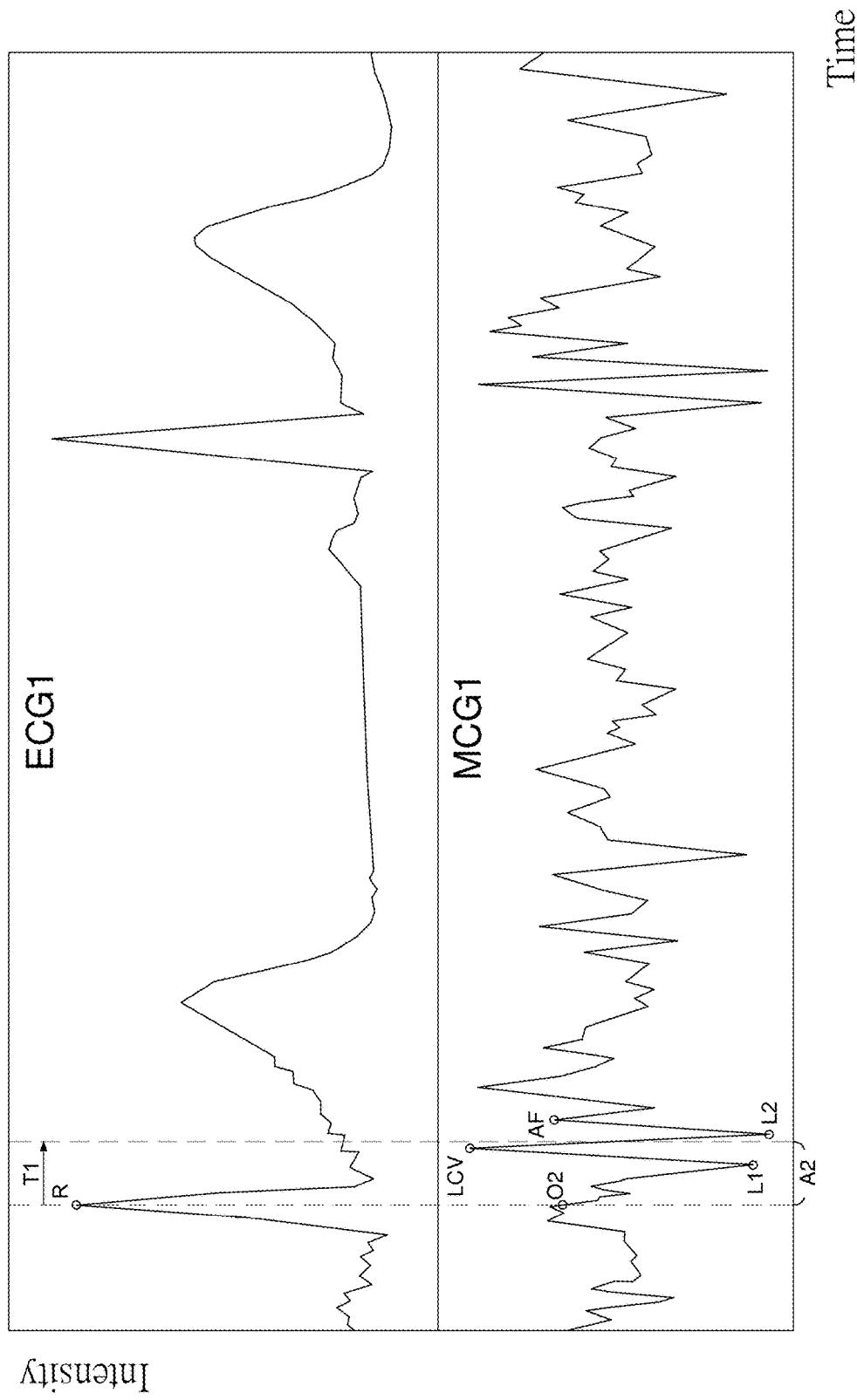
FIG. 14 is the fourth graph showing signal strength versus time of the fourth set of observations according to the present invention.

Refer to FIG. 13 and FIG. 14. These figures represent a flow chart showing steps and a fourth graph showing signal strength versus time of a fourth embodiment, respectively. The unit of the horizontal axis and the unit of the vertical axis of ECG1 and MCG 1 in the fourth graph showing signal strength versus time of this experiment are the same as those in the first graph showing signal strength versus time of the first experiment. The hardware of this experiment is also the same with the above three experiments. The difference between this experiment and the third experiment is only that the feature point AF is obtained in a different way. Similar to the second experiment, this experiment first retrieves the feature point LCV and then finds out the feature point AF located after the feature point LCV. The method of this experiment includes the following steps:

Step S1010: Arrange a gravity sensor at an aortic area on the body surface that corresponds to the heart valves to get a first MCG reading (MCG 1) by the gravity sensor;

Step S1020: Place an ECG sensing module on a lead attachment region on the body surface to get an ECG reading;

Step S1031: Retrieve an R-wave peak of the ECG1 and correspond the R-wave peak to the MCG1 to get a second corresponding point;

Step S1041: Retrieve a valley with the minimum value and a peak thereafter in turn within an interval of 0.06 seconds after the second corresponding point O2. The peak is a lateral wall contraction maximal velocity feature point (LCV); and Step S1043: Retrieve a valley and a peak after the LCV in turn; the peak is a transaortic maximal flow feature point (AF).

Back to FIG. 7, step S1010 and step S1041 are the same as those of the second experiment.

In step S1043, the processor 16 retrieves a valley L2 and a peak after the LCV after the feature point LCV in turn while the peak is a transaortic maximal flow feature point (AF).

After step S1043, the signals are recorded and stored as mentioned in the previous experiment.

The feature point AF of this experiment is at the same position of the MCG 1 as that of the above third experiment. Thereby this experiment can also get the same identification result as the third experiment according to the DG 2.

Figure 15:
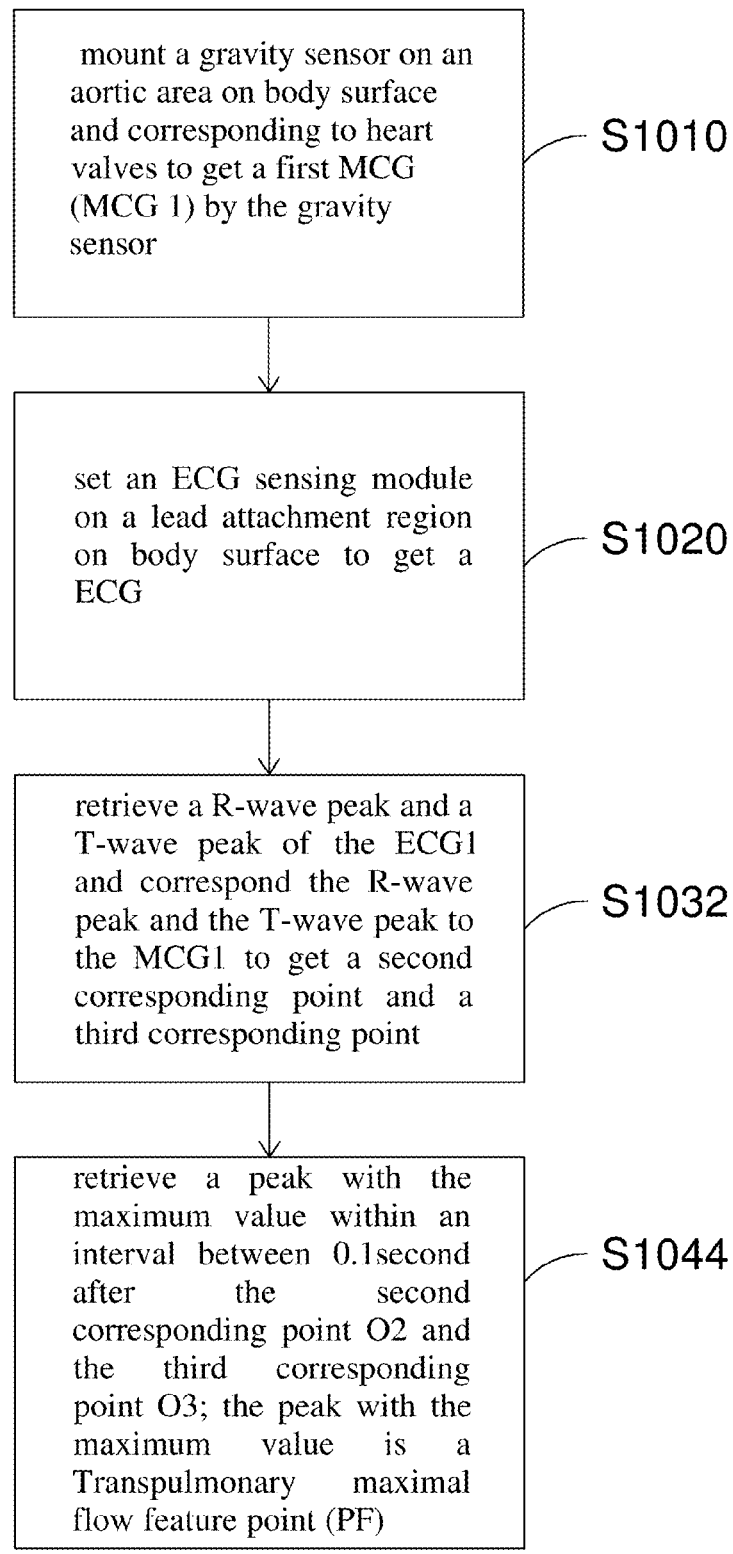
FIG. 15 is the fifth flow chart showing steps of the fifth set of observations according to the present invention.
Figure 16:
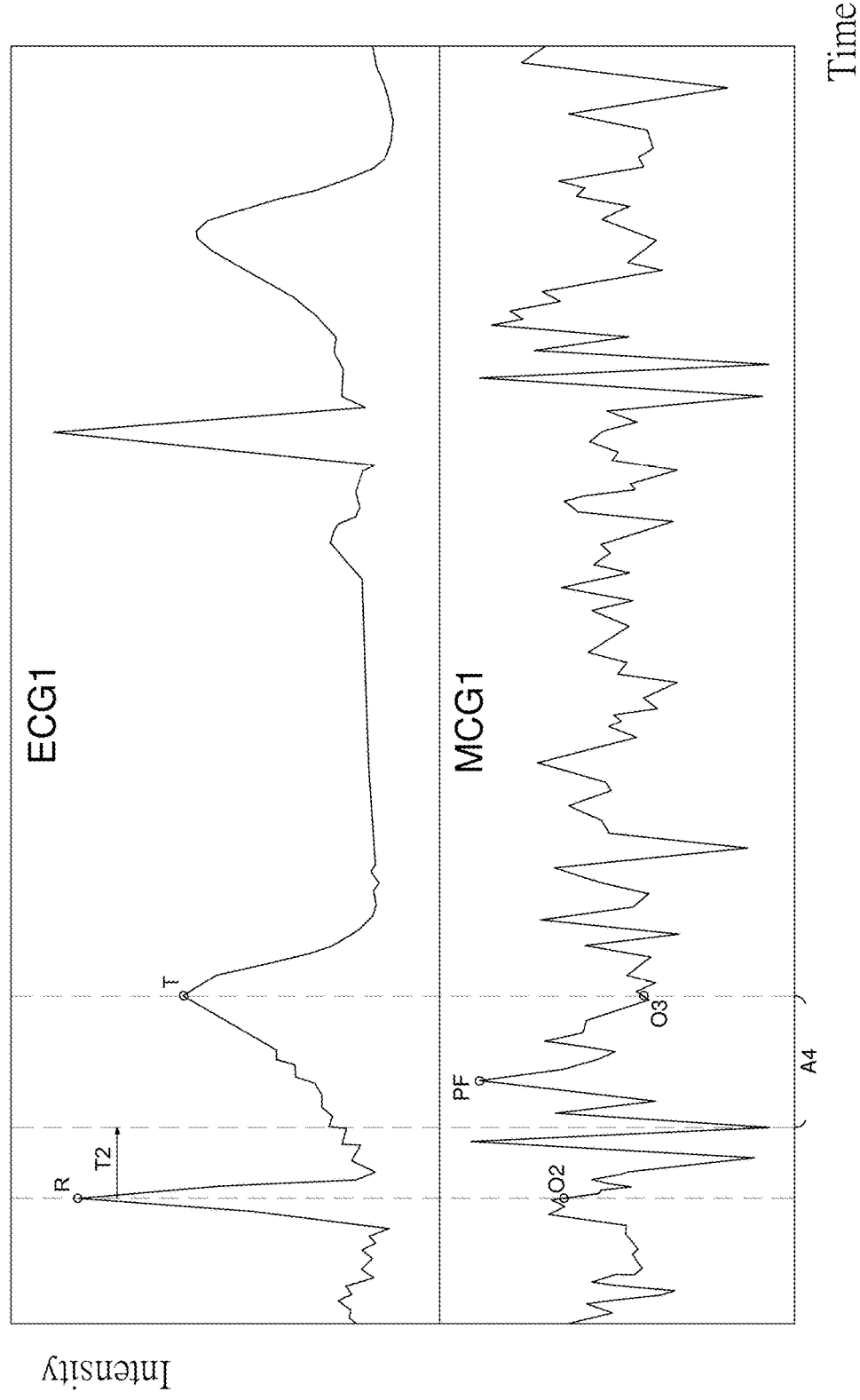
FIG. 16 is the fifth graph showing signal strength versus time of the fifth set of observations according to the present invention.

Refer to FIG. 15 and FIG. 16. These figures are a flow chart showing steps and a fifth graph showing signal strength versus time of a fifth experiment, respectively. The unit of the horizontal axis and the unit of the vertical axis of ECG1 and MCG 1 in the fifth graph showing signal strength versus time of this experiment are the same as those in the first graph showing signal strength versus time of the first experiment. The hardware of this experiment is also the same with the first experiment. The difference between this experiment and the first experiment is only in the retrieving time so that a further feature point is identified. A method of this experiment includes the following steps:

Step S1010: Mount a gravity sensor on an aortic area on the body surface that corresponds to the heart valves to get a first MCG reading (MCG 1) by the gravity sensor;

Step S1020: Set an ECG sensing module on a lead attachment region on the body surface to get an ECG;

Step S1032: Retrieve an R-wave peak and a T-wave peak of the ECG1 that correspond to the R-wave peak and the T-wave peak to the MCG1 to get a second corresponding point and a third corresponding point; and Step S1044: Retrieve a peak with the maximum value within an interval between 0.1 seconds after the second corresponding point O2 and the third corresponding point O3; the peak with the maximum value is a Transpulmonary maximal flow feature point (PF).

Refer to FIG. 7. Step S1010 and step S1020 are the same as those of the second experiment. The step S1032 is similar to step S1031 while one more point (a T-wave peak of ECG1) is retrieved and corresponding to the MCG1 by the processor 16 MCG1 to get a third corresponding point O3.

In step S1044, the processor 16 retrieves several peaks and valleys within a fourth time interval A4 between the second time point T2 after the second corresponding point O2 and the third corresponding point O3 of the MCG 1 to get a peak with the maximum value. The peak with the maximum value is preferred to be at the position of 0.07 seconds after the second corresponding point O2 and representing the transpulmonary maximal flow feature point (PF) while the optimal second time point T2 is 0.1 seconds.

After step S1044, the signals are recorded and stored as mentioned in the previous experiment.

Figure 17:
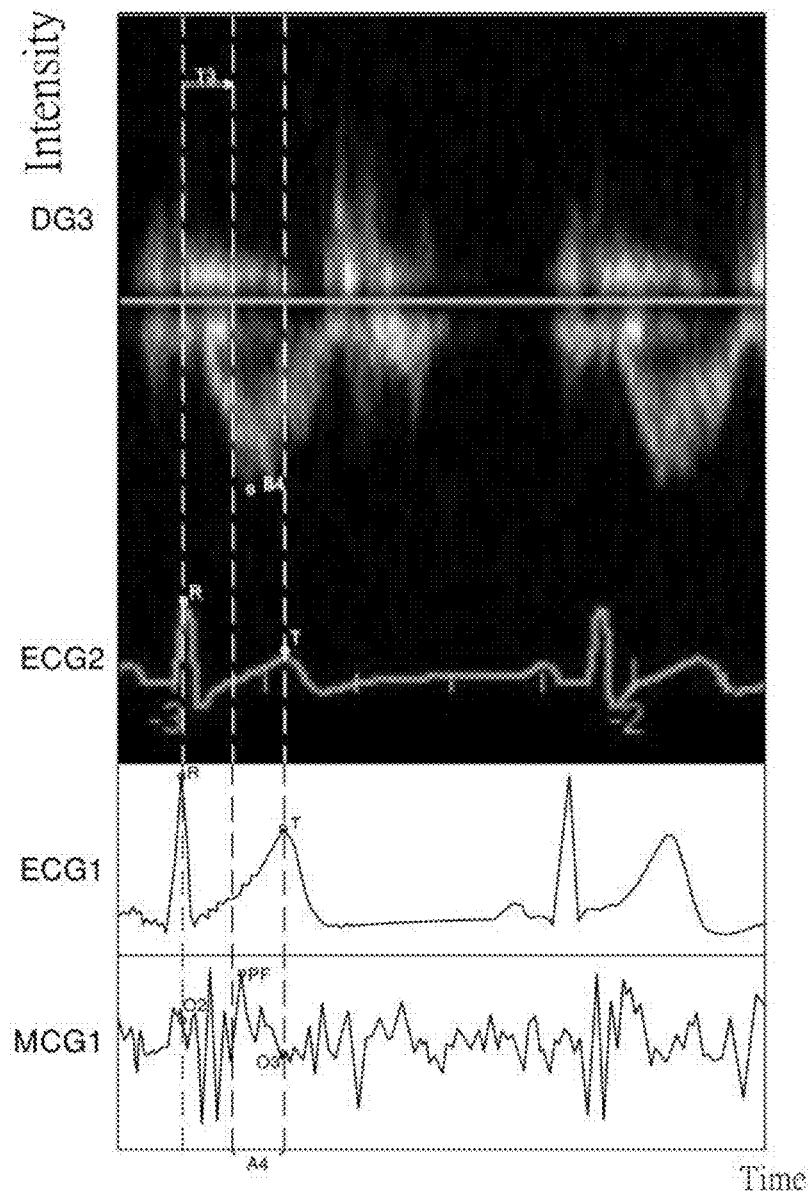
FIG. 17 is the fourth comparative figure showing signal strength versus time of the fifth set of observations according to the present invention.

Refer to FIG. 17. This figure is a fourth comparative figure of a fifth experiment. The unit of the horizontal axis and the unit of the vertical axis of ECG1, ECG2, MCG1 and a third Doppler Echocardiography (DG3) are the same as those of the first graph showing signal strength versus time of the first experiment. In this experiment, a Doppler ultrasonic device the same with the one used in the first experiment is used to get the DG3 while the DG3, MCG1, ECG1 and ECG2 of this experiment are measured at the same time. An ultrasonic transducer of the Doppler ultrasonic device is mounted on the right ventricle area and toward the pulmonary valve to receive vibrations caused by the heartbeat so as to get the DG3 and identify the position of the feature point PF of the MCG1 at the same time.

Refer to the DG3. There is a valley B4 with the minimum value showing maximum blood flow or blood pressure of the right ventricle, which is considered to be identical with the feature point PF by physicians. This is in accordance to the valley B4 with the minimum value and several peaks and valleys in the fourth time interval A4 of the MCG1. Both the valley B4 with the minimum value of the DG3 and the feature point PF of the MCG1 fall in the fourth time interval A4 while the feature point PF is the peak with the maximum value and the valley B4 with the minimum value within the fourth time interval A4. Thus the feature point PF of the MCG1 in this experiment is identical to the valley B4 with the minimum value of the DG3.

Figure 18:
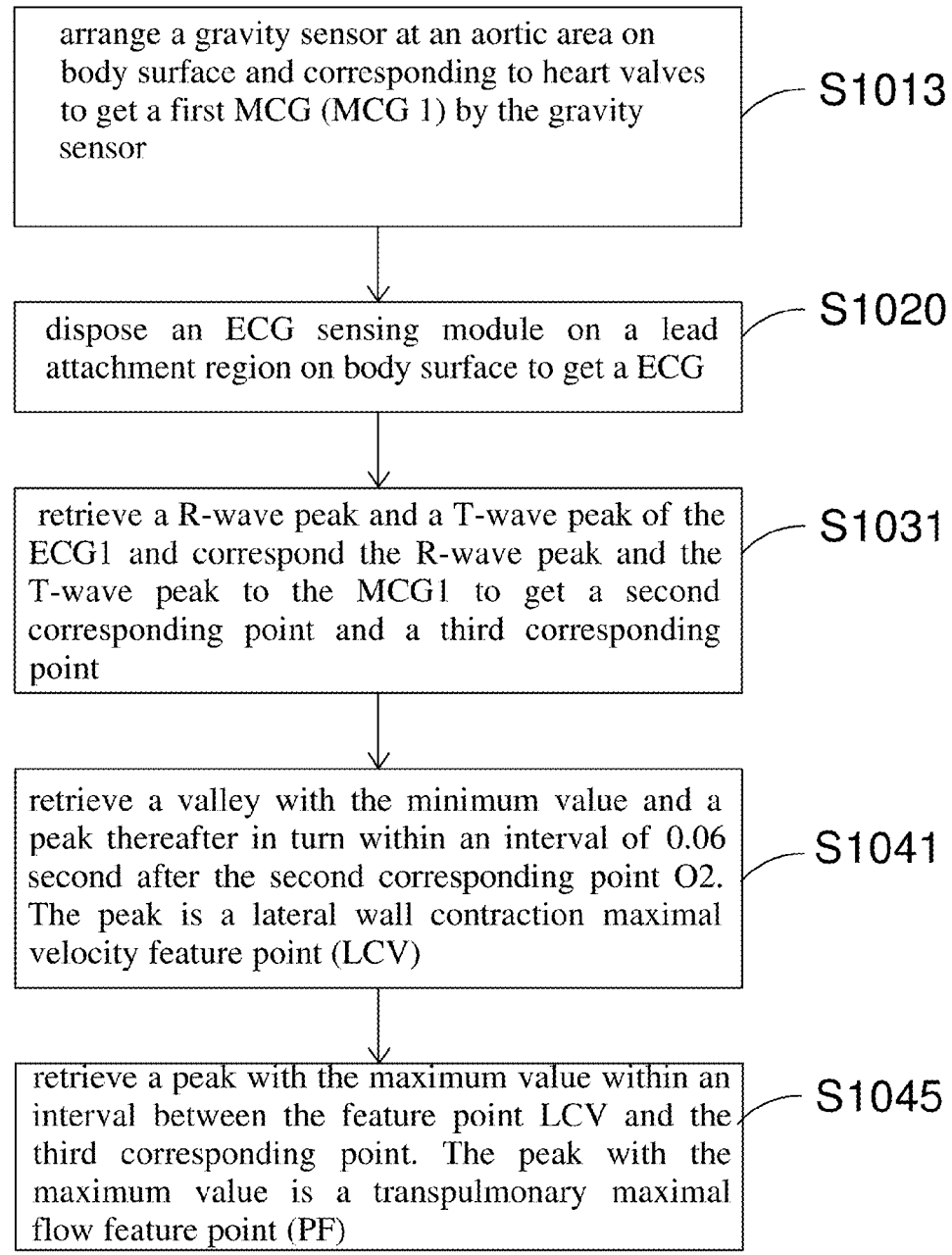
FIG. 18 is the sixth flow chart showing steps of the sixth set of observations according to the present invention.
Figure 19:
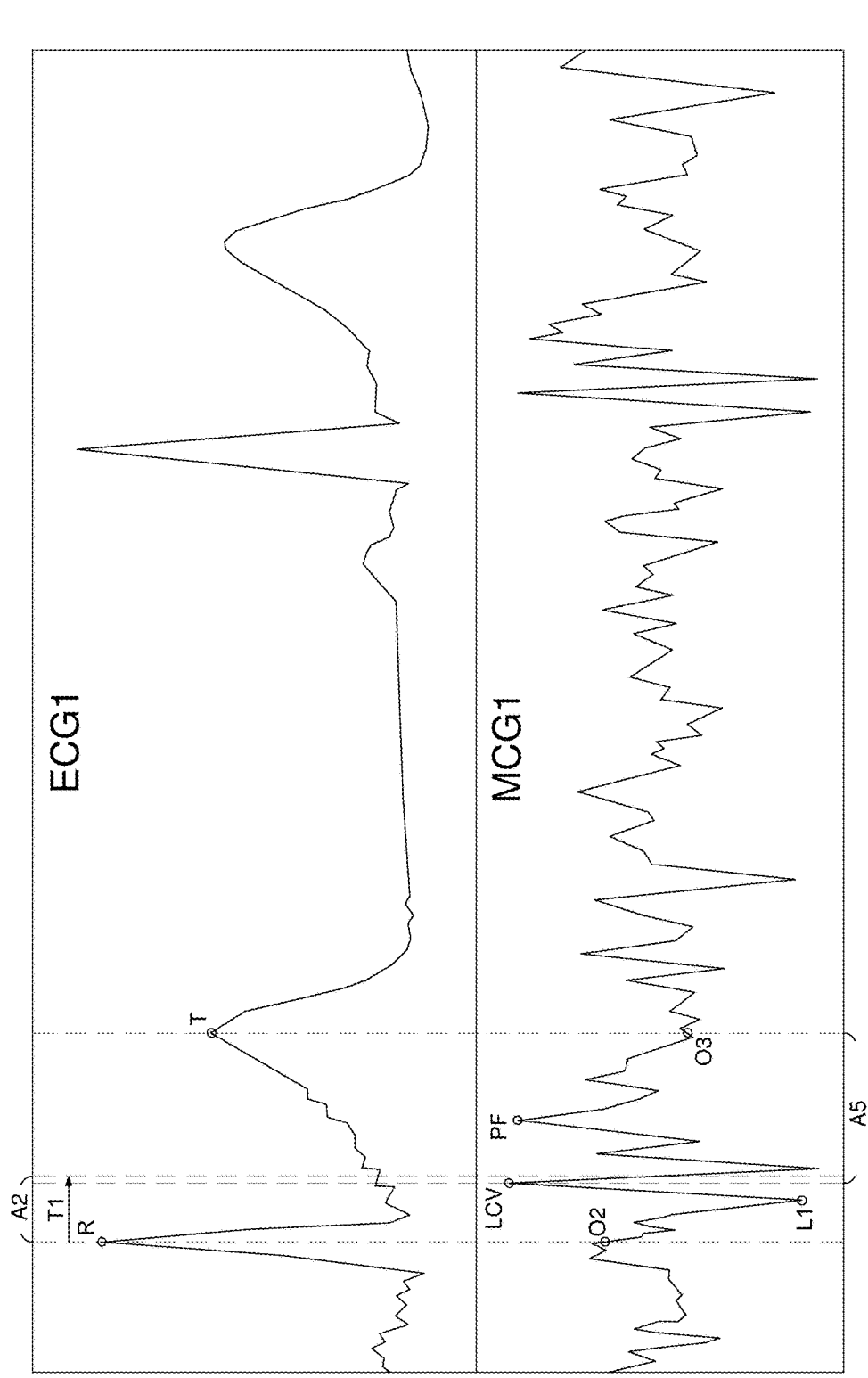
FIG. 19 is the sixth graph showing signal strength versus time of the sixth set of observations according to the present invention.

Refer to FIG. 18 and FIG. 19. These figures are a flow chart showing steps and a sixth graph showing signal strength versus time of a sixth experiment, respectively. The unit of the horizontal axis and the unit of the vertical axis of ECG1 and MCG 1 in the sixth graph showing signal strength versus time of this experiment are the same as those in the first graph showing signal strength versus time of the first experiment. The hardware of this experiment is also the same with the above 5 experiment. The difference between this experiment and the fifth experiment is only in that the feature point PF is obtained in a different way. Similar to the second experiment, this experiment first retrieves the feature point LCV and then finds out the feature point PF located after the feature point LCV. The method of this experiment includes the following steps:

Step S1010: Arrange a gravity sensor at an aortic area on the body surface that corresponds to the heart valves to get a first MCG reading (MCG 1) by the gravity sensor;

Step S1020: Place an ECG sensing module on a lead attachment region on the body surface to get a ECG;

Step S1032: Retrieve an R-wave peak and a T-wave peak of the ECG1 that corresponds to the R-wave peak and the T-wave peak to the MCG1 to get a second corresponding point and a third corresponding point;

Step S1041: Retrieve a valley with the minimum value and a peak thereafter in turn within an interval of 0.06 seconds after the second corresponding point. The peak is a lateral wall contraction maximal velocity feature point (LCV).

Step S1045: Retrieve a peak with the maximum value within an interval between the feature point LCV and the third corresponding point. The peak with the maximum value is a transpulmonary maximal flow feature point (PF).

Refer to FIG. 7 and FIG. 15. Steps S1010, S1020, and S1041 are the same as those of the second experiment while step S1032 is the same as that of the fifth experiment.

In step S1045, the processor 16 retrieves several peaks and valleys within a fifth time interval A5 between the feature point LCV and the third corresponding point O3 of the MCG1 to get the peak with the maximum value. The peak with the maximum value represents the feature point PF.

After step S1045, the signals are recorded and stored as mentioned in the previous experiment.

The feature point PF is at the same position of the MCG1 as the fifth experiment. Thus the DC3 also have the same identification results as those of the fifth experiment.

Figure 20:
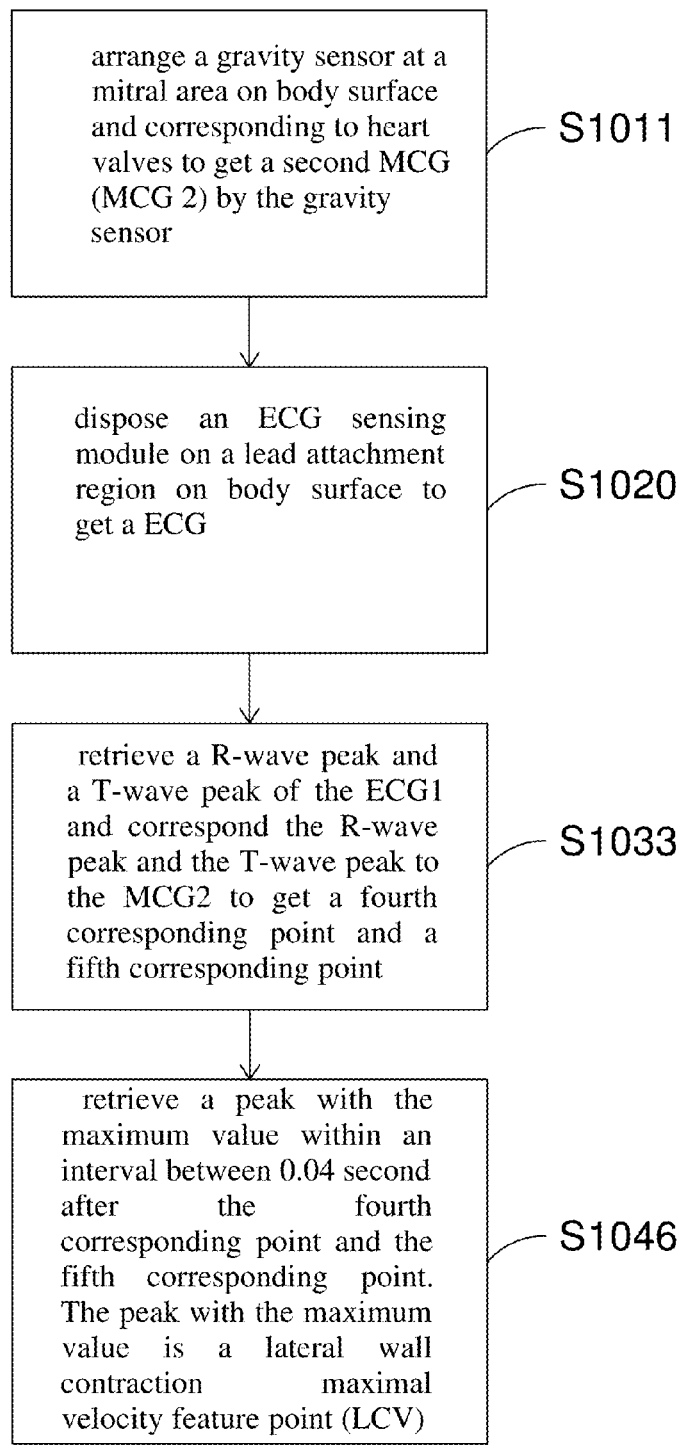
FIG. 20 is the seventh flow chart showing steps of the seventh set of observations according to the present invention.
Figure 21:
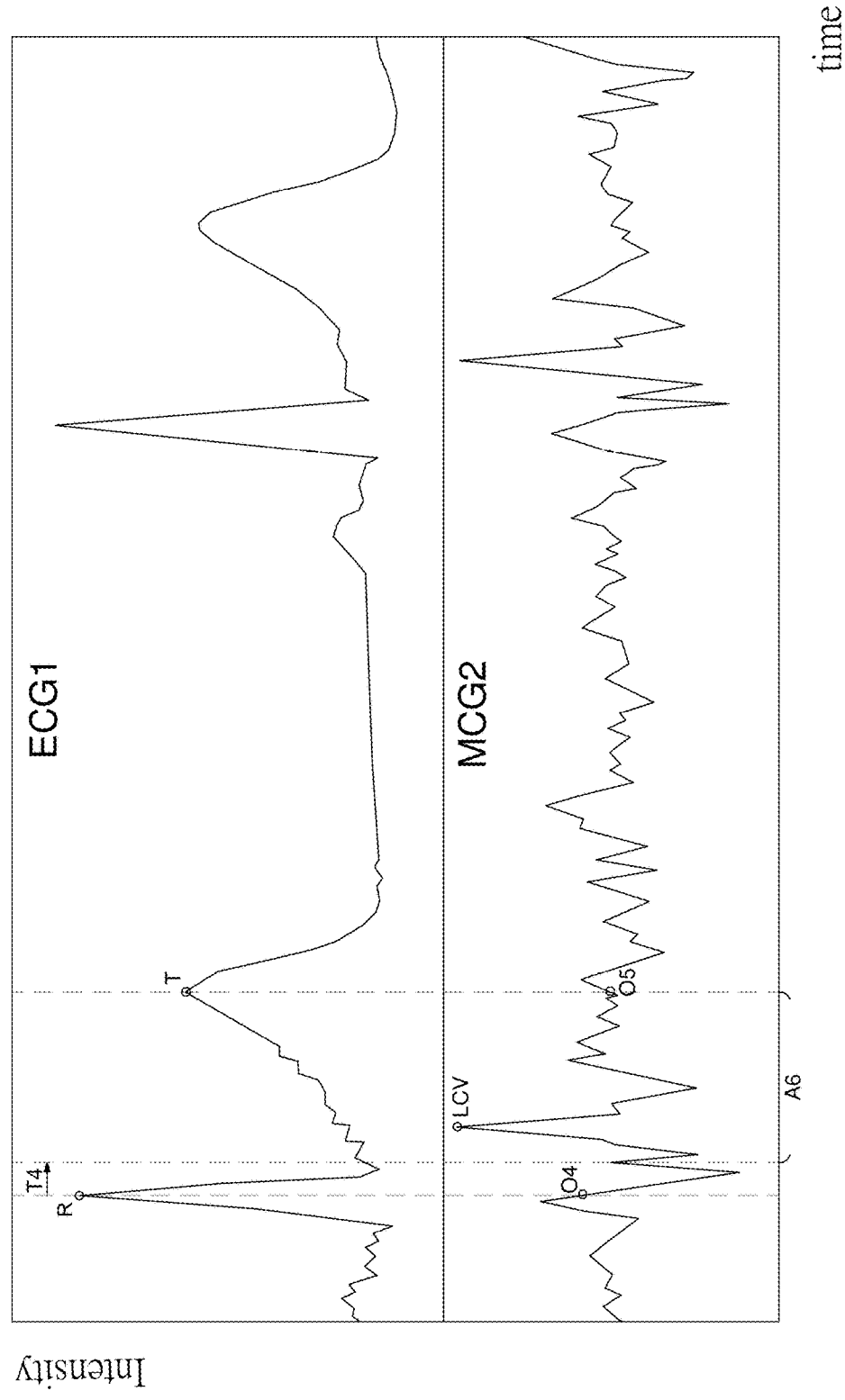
FIG. 21 is the seventh graph showing signal strength versus time of the seventh set of observations according to the present invention.

Refer to FIG. 20 and FIG. 21. These figures are a flow chart showing steps and a seventh graph showing signal strength versus time of a seventh experiment, respectively. The unit of the horizontal axis and the unit of the vertical axis of ECG1 and MCG 2 in the seventh graph showing signal strength versus time of this experiment are the same as those in the first signal-time graph of the first experiment. The hardware of this experiment is almost the same with the first experiment, only different in the position of the gravity sensor 12 (refer to FIG. 1) and the retrieving time is different to get another feature point such as LCV of the second experiment. The method of this experiment includes the following steps:

Step S1011: Arrange a gravity sensor at the mitral area on the body surface that corresponds to the heart valves to get a second MCG reading (MCG 2) by the gravity sensor;

Step S1020: Place an ECG sensing module on a lead attachment region on the body surface to get a ECG;

Step S1033: Retrieve an R-wave peak and a T-wave peak of the ECG1 and correspond the R-wave peak and the T-wave peak to the MCG2 to get a fourth corresponding point and a fifth corresponding point; and Step S1046: Retrieve a peak with the maximum value within an interval between 0.04 seconds after the fourth corresponding point and the fifth corresponding point. The peak with the maximum value is a lateral wall contraction maximal velocity feature point (LCV).

As shown in FIG. 1 and FIG. 3, in step S1011, the gravity sensor 12 placed on the mitral area 32 is used for receiving vibrations on the body surface at the mitral area 32 caused by the heartbeat to get a second MCG reading (MCG2).

Back to FIG. 4, step S1020 of this experiment is the same as that of the first experiment.

Refer to FIG. 15. Step S1033 of this experiment is similar to step S1032 of the fifth experiment. The difference is only that the R-wave peak and the T-wave peak correspond to the MCG2 to get a fourth corresponding point O4 and a fifth corresponding point O5 of the MCG2. The horizontal axis (time) of the ECG1 and the horizontal axis (time) of the MCG2 are dependent.

In step S1046, the processor 16 retrieves several peaks and valleys in a sixth time interval A6 between a fourth time point T4 after the fourth corresponding point O4 and the fifth corresponding point O5 of the MCG 2 to get a peak with the maximum value. The peak with the maximum value is a transpulmonary maximal flow feature point (PF), at the position of 0.07 seconds after the fourth corresponding point O4. The optimal fourth time point T4 is 0.04 seconds.

After step S1046, the signals are recorded and stored as mentioned in the above experiment.

Figure 22:
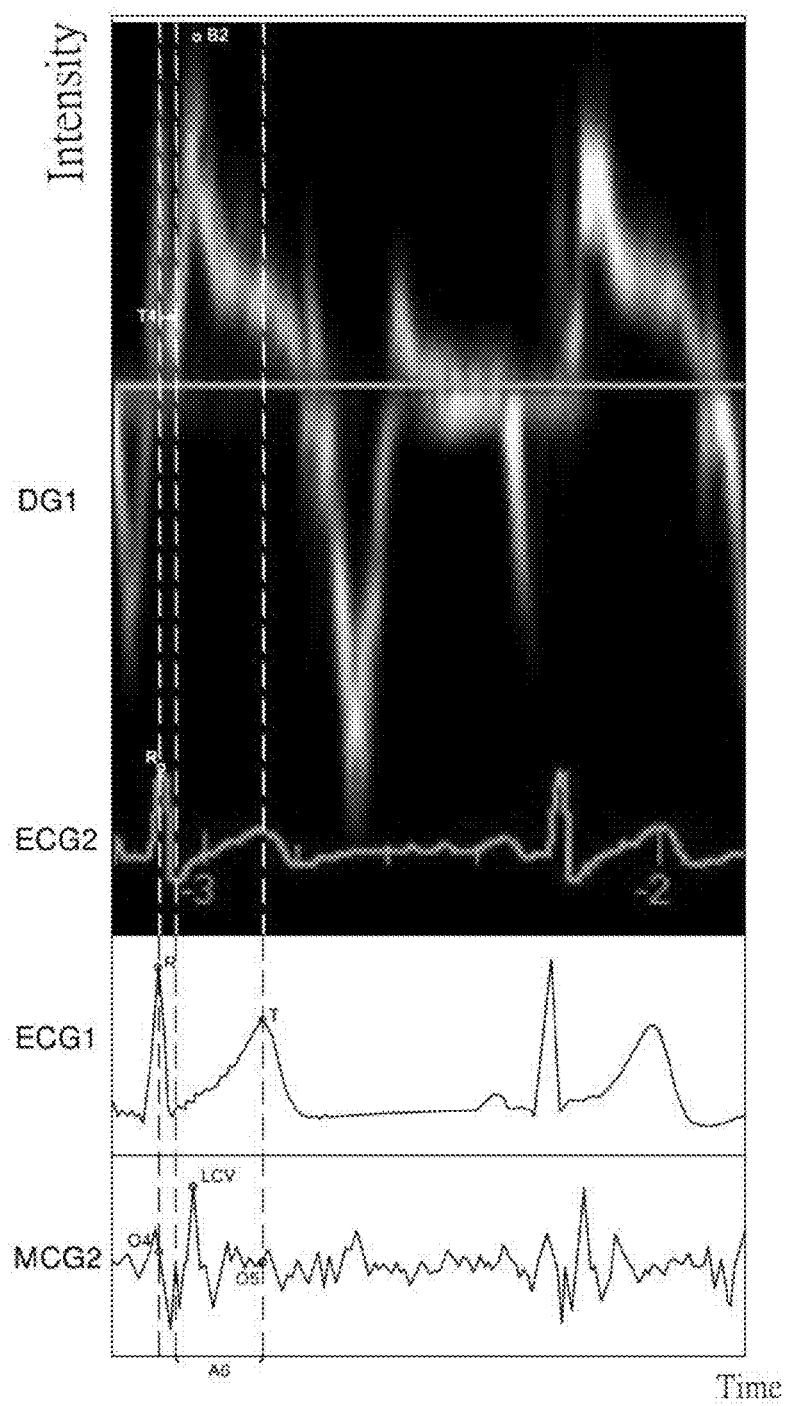
FIG. 22 is the fifth comparative figure showing signal strength versus time of the seventh set of observations according to the present invention.

Refer to FIG. 22. This figure depicts a fifth comparative figure of a seventh experiment. The unit of the horizontal axis and the unit of the vertical axis of ECG1, ECG2, MCG2 and the first Doppler Echocardiography (DG1) are the same as those of the first graph showing signal strength versus time of the first experiment. In this experiment, a Doppler ultrasonic device identical to the device used in the second experiment is used to detect heartbeat-induced vibrations on the body surface so as to identify the position of the feature point LCV of the MCG2 at the same time. The DG1, MCG2, ECG1 and ECG2 of this experiment are measured at the same time. According to the peak B2 with the maximum value and the peaks and the valleys in the sixth time interval A6 of the MCG2, both the feature point LCV of the MCG2 and the peak B2 with the maximum value are falling into the sixth time interval A6 of the MCG2 and having the maximum value in the sixth time interval A6. Thus the feature point LCV of the MCG2 and the peak B2 with the maximum value of the DG1 are identical to each other.

Figure 23:
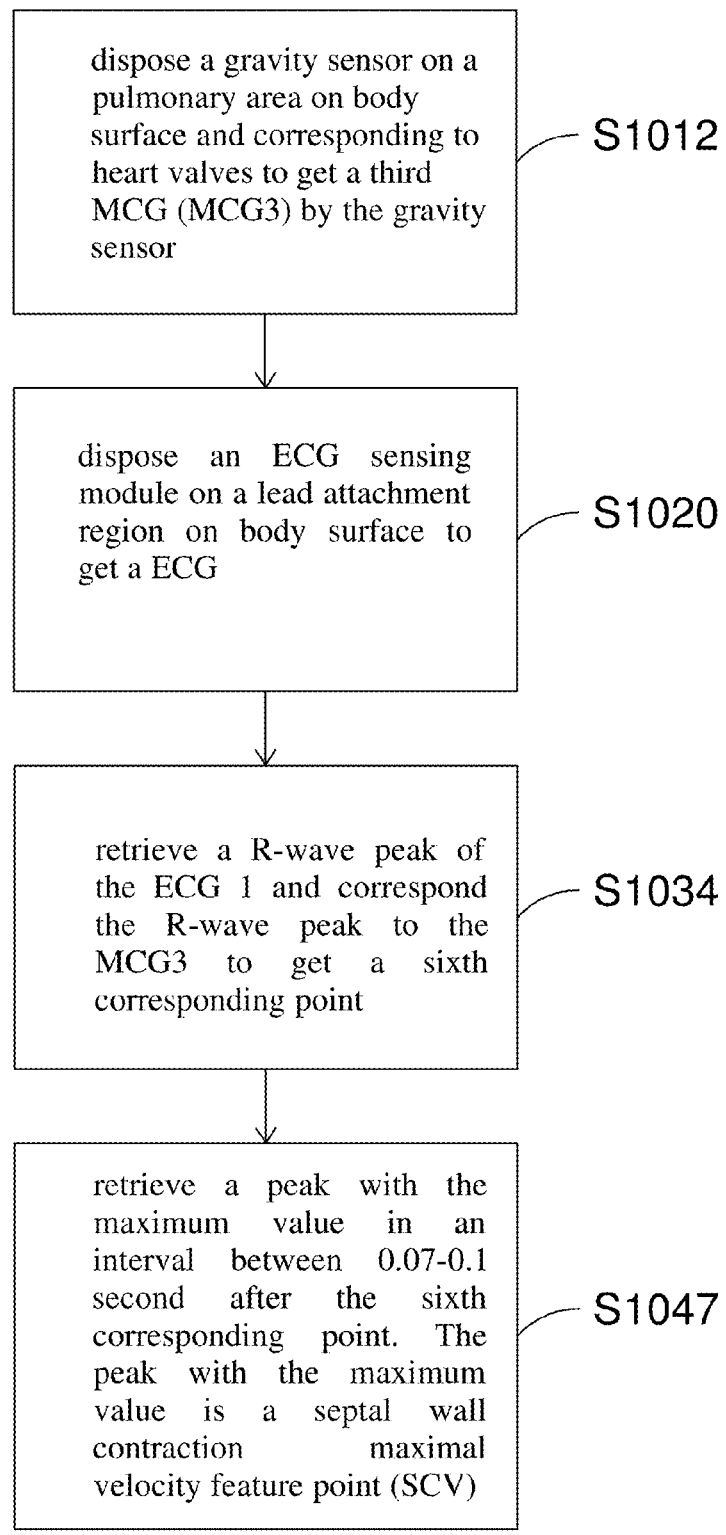
FIG. 23 is the eighth flow chart showing steps of the eighth set of observations according to the present invention.
Figure 24:
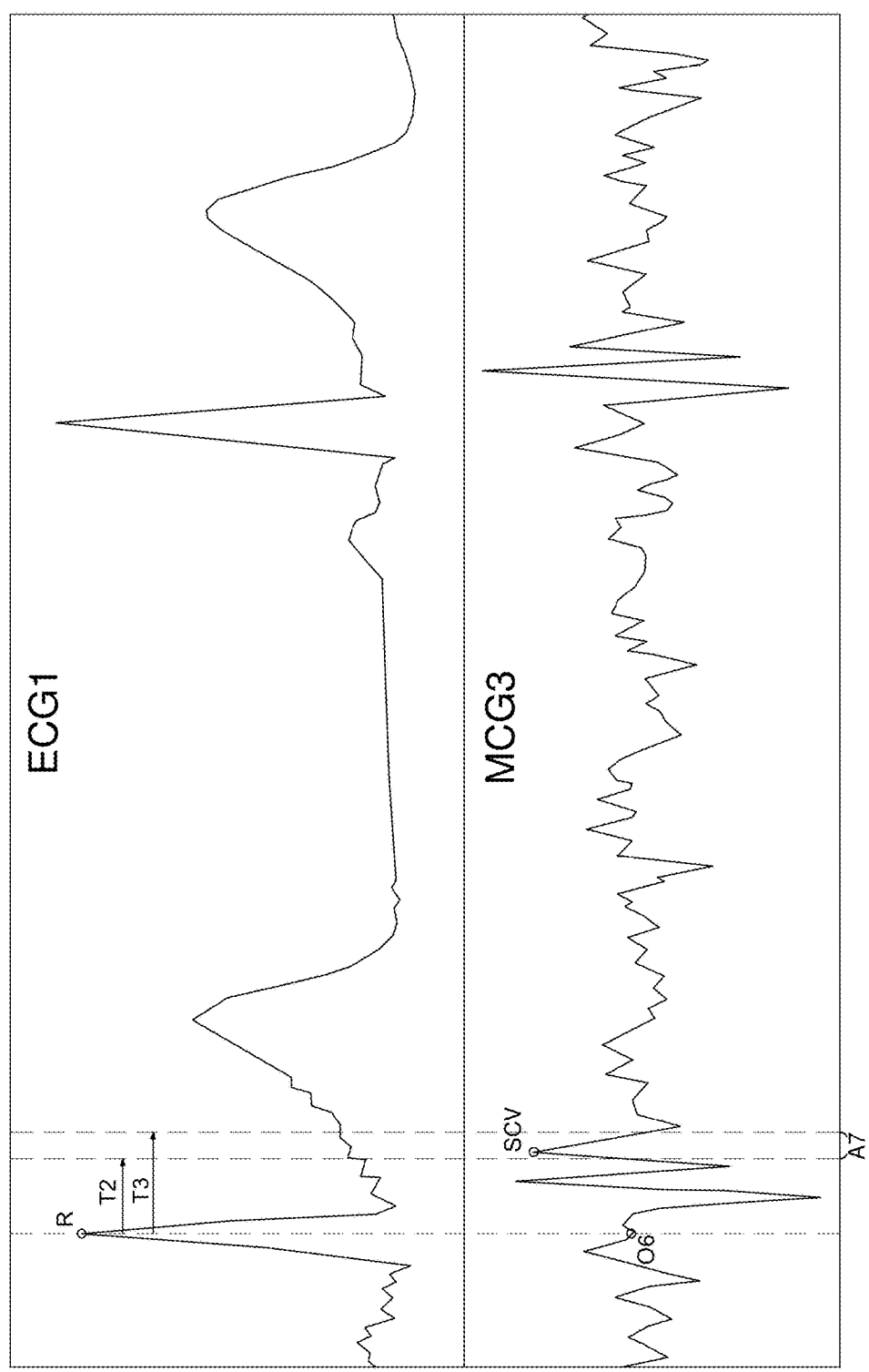
FIG. 24 is the eighth graph showing signal strength versus time of the eighth set of observations according to the present invention.

Refer to FIG. 23 and FIG. 24. These figures depict a flow chart showing steps and an eighth graph showing signal strength versus time of an eighth experiment, respectively. The unit of the horizontal axis and the unit of the vertical axis of ECG1 and MCG 3 in the eighth graph showing signal strength versus time of this experiment are the same as those in the first graph showing signal strength versus time of the first experiment. The hardware of this experiment is also the same as the first experiment. The difference between this experiment and the first experiment includes the position of the gravity sensor 13 and the retrieving time so that a further feature point is discovered. The method of this experiment includes the following steps:

Step S1012: Place a gravity sensor on the pulmonary area of the body surface that corresponds to the heart valves to get a third MCG reading (MCG3) by the gravity sensor;

Step S1020: Place an ECG sensing module on a lead attachment region on the body surface to get an ECG;

Step S1034: Retrieve an R-wave peak of the ECG 1 that corresponds to the R-wave peak to the MCG3 to get a sixth corresponding point.

Step S1047: Retrieve a peak with the maximum value in an interval between 0.07-0.1 seconds after the sixth corresponding point. The peak with the maximum value is a septal wall contraction maximal velocity feature point (SCV).

Refer to FIG. 1 and FIG. 3. In step S1012, the gravity sensor 13 arranged at the pulmonary area 33 is used for receiving vibrations on the body surface at the pulmonary area 33 caused by heartbeat to get a third MCG reading (MCG3).

Refer to FIG. 4. Step S1020 of this experiment is the same as that of the first experiment.

Refer to FIG. 7. Step S1034 of this experiment is similar to step S1031 of the second experiment. The difference is that this experiment the R-wave peak of the ECG1 corresponds to the MCG3 to get a sixth corresponding point O6 of the MCG3. The horizontal axis (time) of the ECG1 and the horizontal axis (time) of the MCG3 are dependent.

In step S1047, the processor 16 retrieves several peaks and valleys within a seventh time interval A7 between a second time point T2 and a third time point T3 after the sixth corresponding point O6 of the MCG 3 to get a peak with the maximum value. The peak with the maximum peak value is preferred to be at the position of 0.082 seconds after the sixth corresponding point O6 and is representing a septal wall contraction maximal velocity feature point (SCV).

After step S1047, the signals are recorded and stored as mentioned previously.

Figure 25:
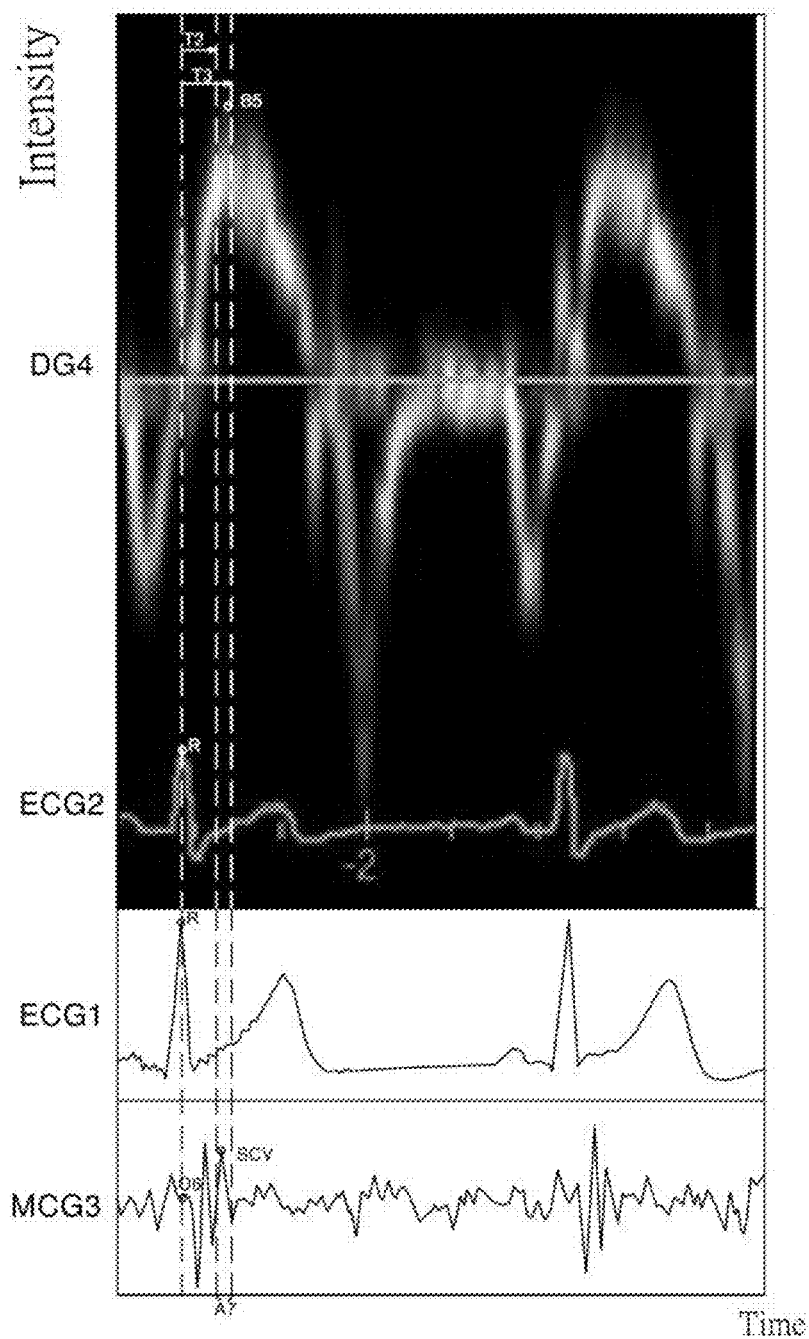
FIG. 25 is the sixth comparative figure showing signal strength versus time of the eighth set of observations according to the present invention.

Refer to FIG. 25. This figure is the sixth comparative figure of a eighth experiment. The unit of the horizontal axis and the unit of the vertical axis of ECG1, ECG2, MCG1 and a fourth Doppler Echocardiography (DG4) are the same as those of the first graph showing signal strength versus time of the first experiment. In this experiment, a Doppler ultrasonic device similar to that used in the third experiment is used and the ultrasonic transducer of the Doppler ultrasonic device is mounted at the same position while the DG4, MCG3, ECG1 and ECG2 of this experiment are also measured at the same time. The difference is that the ultrasonic transducer is placed toward the septal wall to get the DG4 and identify the position of the feature point SCV of the MCG3 at the same time.

Refer to the DG4. There is a peak B5 with the maximum value that shows the maximal velocity of the septal wall, which considered to be identical with the feature point LCV by physicians. This is in accordance to the peak B5 with the maximum value and a seventh time interval A7 of the MCG3. Both the feature point SCV of the MCG3 and the peak B5 with the maximum value of the DG4 fall in the seventh time interval A7 and are with the maximum value in the seventh time interval A7. Thus the feature point SCV of the MCG3 and the peak B5 with the maximum value of the DG4 are identical to each other.

Figure 26:
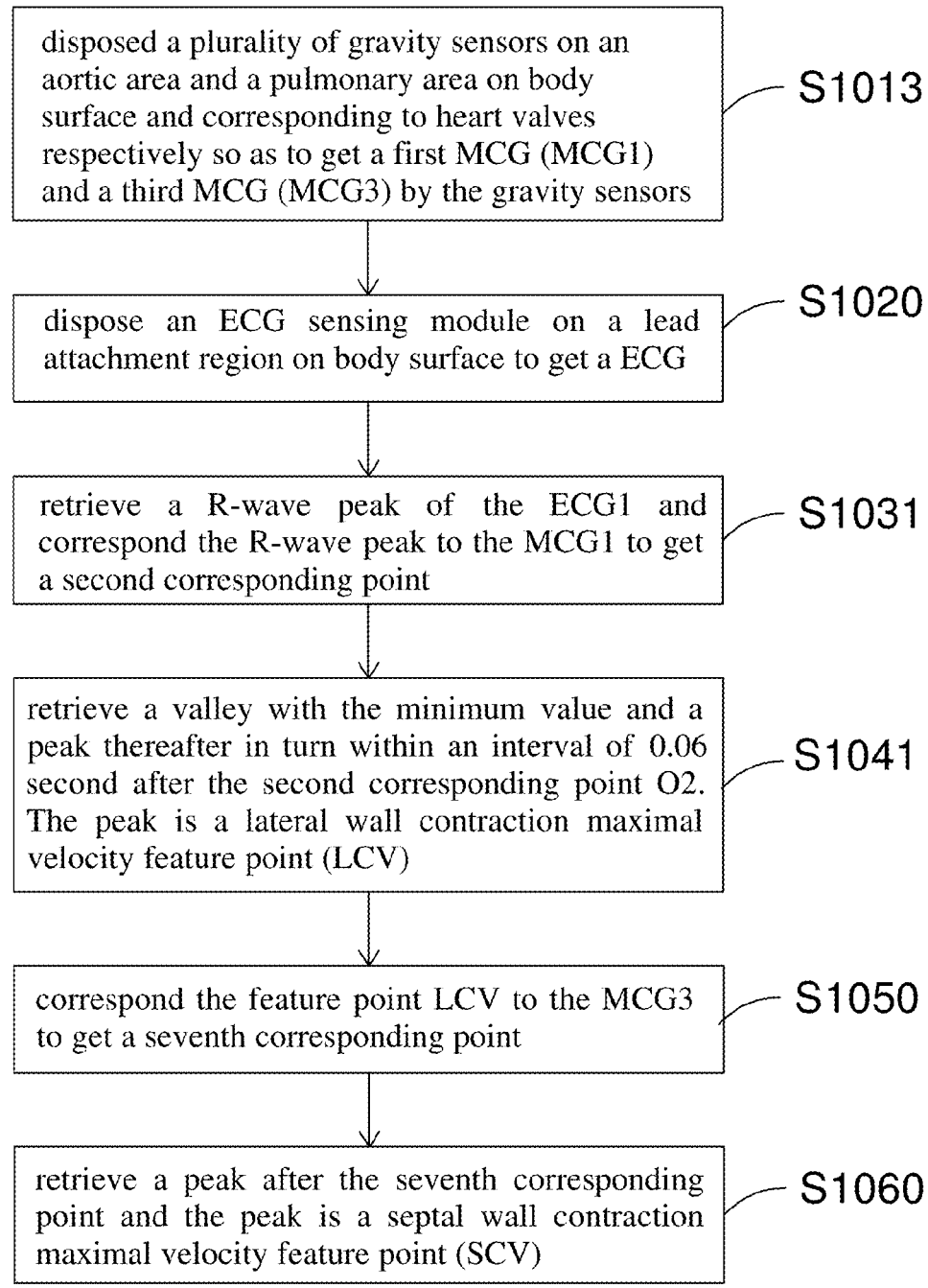
FIG. 26 is the ninth flow chart showing steps of the ninth set of observations according to the present invention.
Figure 27:
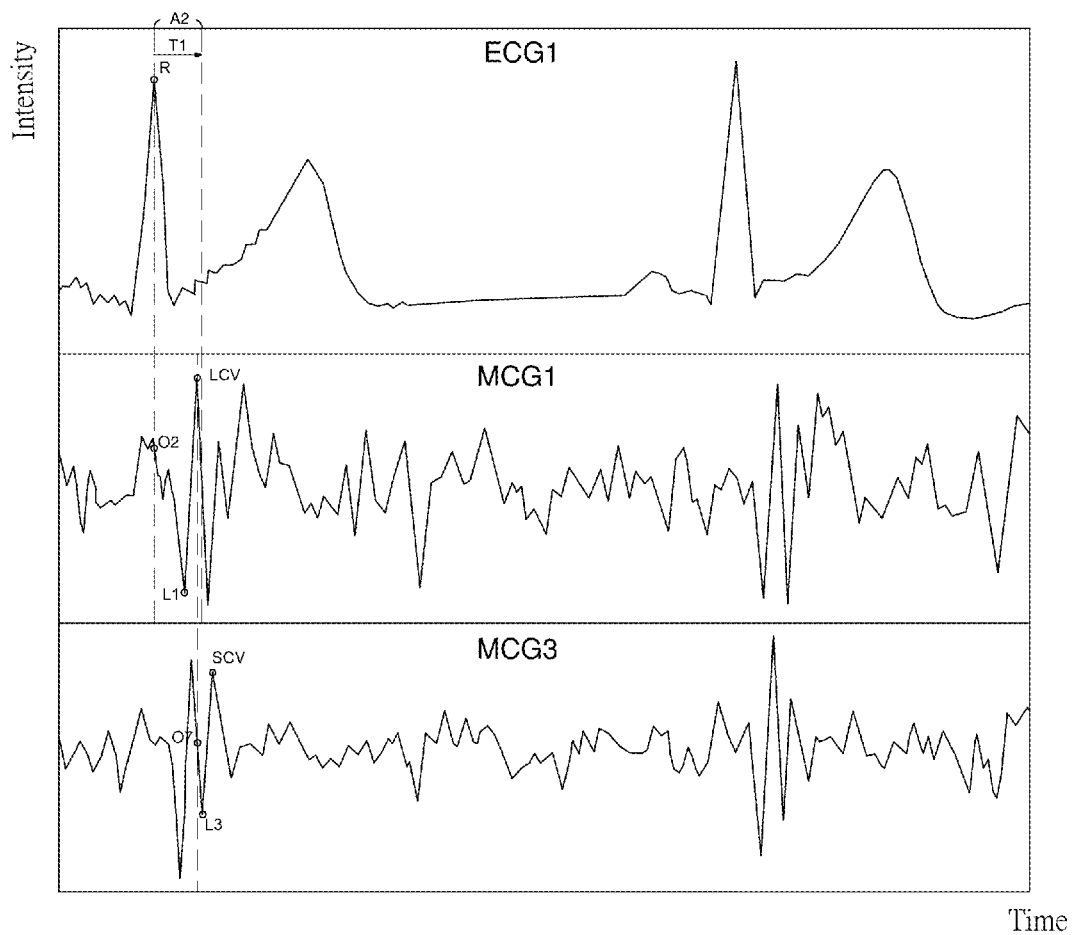
FIG. 27 is the ninth graph showing signal strength versus time of the ninth set of observations according to the present invention.

Refer to FIG. 26 and FIG. 27. These figures are a flow chart showing steps and a ninth graph showing signal strength versus time of a ninth experiment, respectively. The unit of the horizontal axis and the unit of the vertical axis of ECG1, MCG 1 and MCG3 in the ninth graph showing signal strength versus time of this experiment are the same as those in the first graph showing signal strength versus time of the first experiment. The hardware of this experiment is the same as the eighth experiment and only the method to obtain the feature point SCV differs. As in the second experiment, this experiment first retrieves the feature point LCV, then finds out the feature point SCV after the feature point LCV. The method of this experiment includes the following steps:

Step S1013: Place several gravity sensors on the aortic area and the pulmonary area on the body surface that correspond to the heart valves so as to get a first MCG reading (MCG1) and a third MCG reading (MCG3) via the gravity sensors;

Step S1020: Place an ECG sensing module on a lead attachment region on the body surface to get an ECG;

Step S1031: Retrieve an R-wave peak of the ECG1 and correspond the R-wave peak to the MCG1 to get a second corresponding point;

Step S1041: Retrieve a valley with the minimum value and a peak thereafter in turn within an interval of 0.06 seconds after the second corresponding point O2. The peak is a lateral wall contraction maximal velocity feature point (LCV);

Step S1050: Correspond the feature point LCV to the MCG3 to get a seventh corresponding point; and Step S1060: Retrieve a peak after the seventh corresponding point. This peak is a septal wall contraction maximal velocity feature point (SCV).

Refer to FIG. 7 and FIG. 23. Step S1013 of this experiment is the same as step S1010 of the second experiment combined with step S1012 of the eighth experiment. Step S1020, step S1031, and step S1041 of this experiment are the same as those of the second experiment.

In step S1050, the processor 16 corresponds the feature point LCV of the MCG 1 to the MCG3 to get the seventh corresponding point O7. The MCG1 and the MCG3 are time dependent.

In step S1060, the processor 16 retrieves a valley L3 and a peak after the seventh corresponding point O7 of the MCG3 in turn that represents the feature point SCV.

After step S1060, the signals are recorded and stored as mentioned in the previous experiment.

The SCV of this experiment is at the same position of the MCG3 as the eighth experiment. Thus the DGS also displays similar results as those of the eighth experiment.

Figure 28:
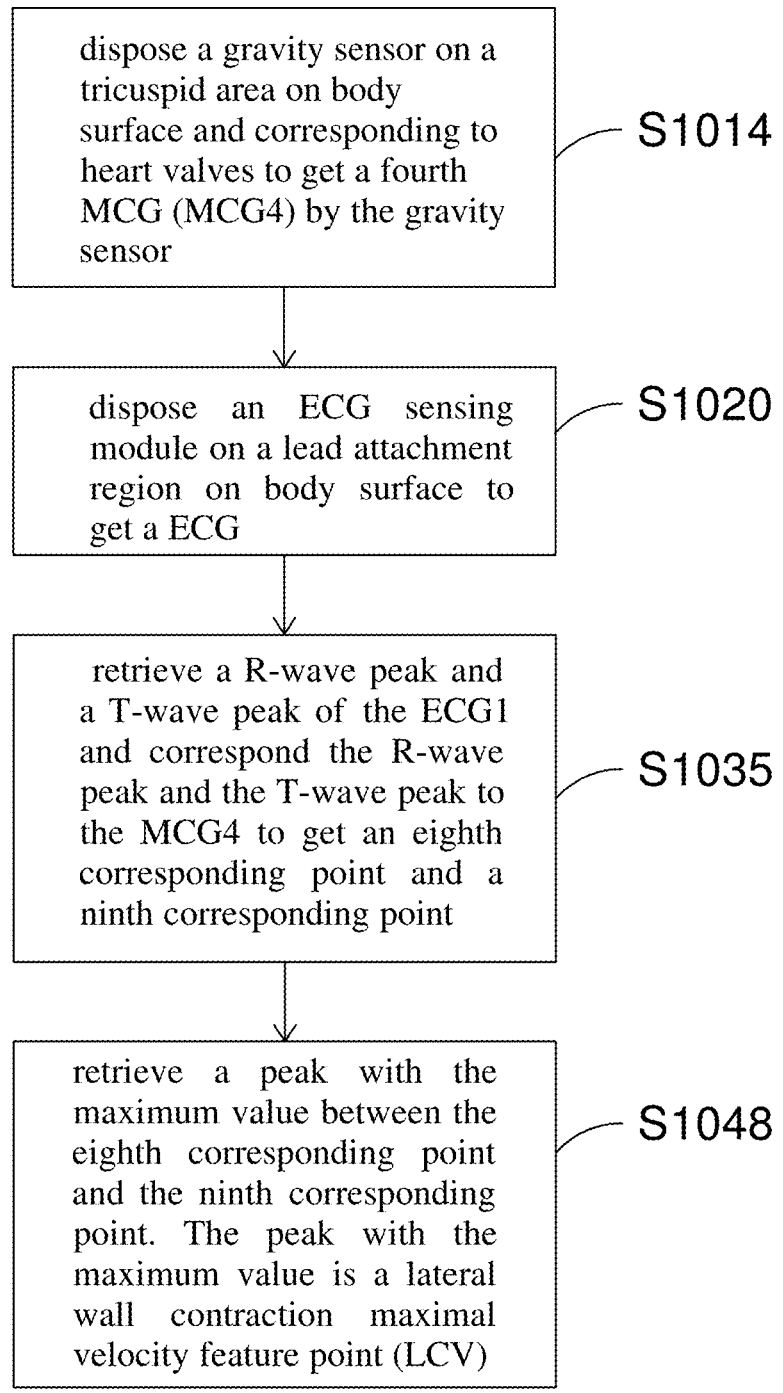
FIG. 28 is the tenth flow chart showing steps of the tenth set of observations according to the present invention.
Figure 29:
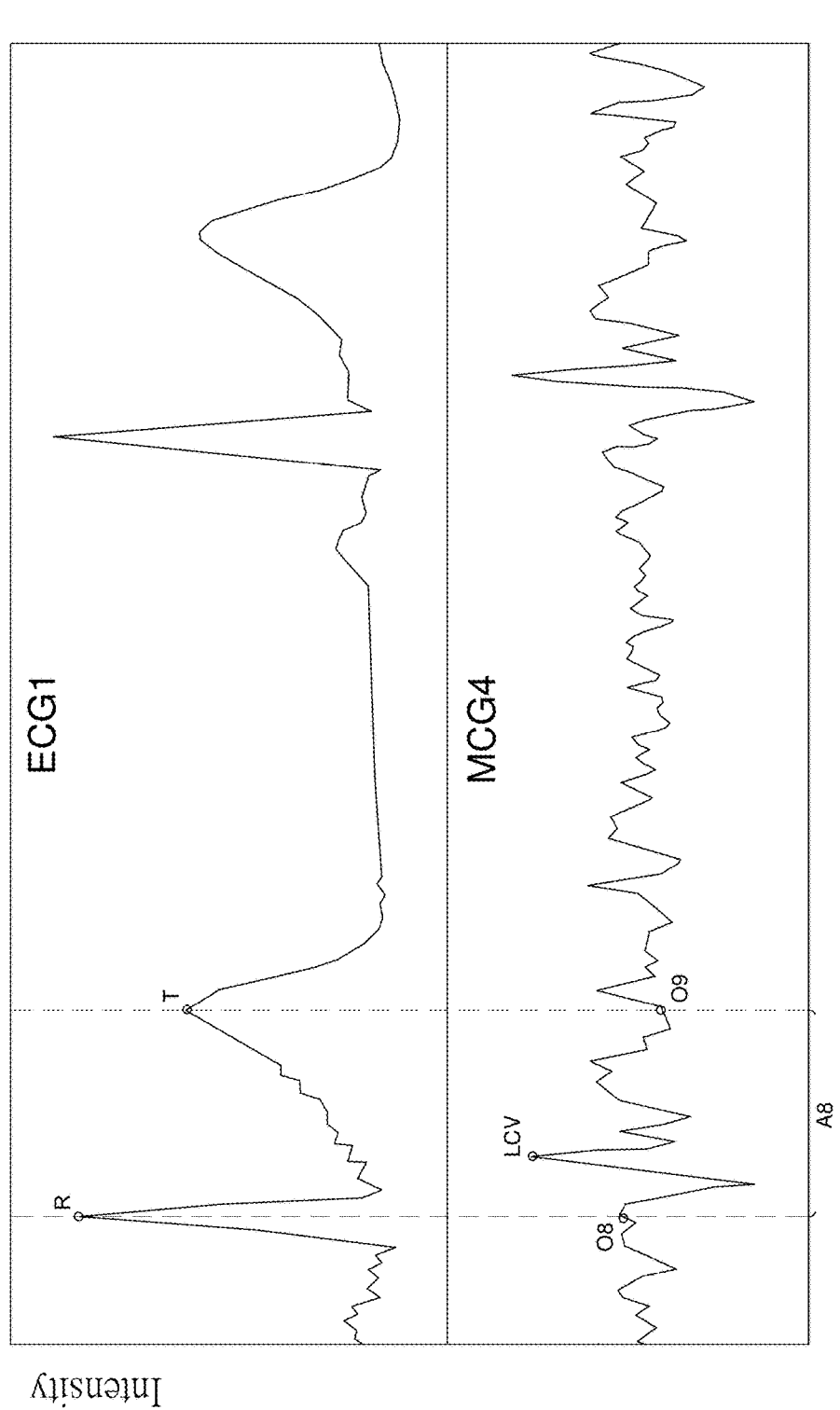
FIG. 29 is the tenth graph showing signal strength versus time of the tenth set of observations according to the present invention.

Refer to FIG. 28 and FIG. 29. These figures depict a flow chart showing steps and a tenth graph showing signal strength versus time of a tenth experiment, respectively. The unit of the horizontal axis and the unit of the vertical axis of ECG1 and MCG 4 in the tenth graph showing signal strength versus time of this experiment are the same as those in the first graph showing signal strength versus time of the first experiment. The hardware of this experiment is also the same as the first experiment. The difference between this experiment and other experiments is that this experiment obtains a feature point similar to the feature point LCV of the second experiment (in FIG. 8). The method of this experiment includes the following steps:

Step S1014: Place a gravity sensor on the tricuspid area on the body surface that corresponds to the heart valves to get a fourth MCG (MCG4) by the gravity sensor;

Step S1020: Place an ECG sensing module on a lead attachment region on the body surface to get a ECG;

Step S1035: Retrieve an R-wave peak and a T-wave peak of the ECG1 that correspond to the R-wave peak and the T-wave peak to the MCG4 to get an eighth corresponding point and a ninth corresponding point.

Step S1048: Retrieve a peak with the maximum value between the eighth corresponding point and the ninth corresponding point. The peak with the maximum value is a lateral wall contraction maximal velocity feature point (LCV).

Refer to FIG. 1 and FIG. 3. In step S1014, the gravity sensor 14 arranged at the tricuspid area 34 is used for receiving vibrations on the body surface at the tricuspid area 34 caused by the heartbeat to get a fourth MCG reading (MCG4). As in step S1020, this is the same the procedure is the same as that of the first experiment.

In step S1035, the processor 16 retrieves the R-wave peak and the T-wave peak of the ECG1 and correspond the R-wave peak and the T-wave peak to the MCG4 to get an eighth corresponding point O8 and a ninth corresponding point O9 of the MCG4. The horizontal axis (time) of the ECG1 and the horizontal axis (time) of the MCG4 are dependent.

In step S1048, the processor 16 retrieves several peaks and valleys within an eighth time interval A8 between the eighth corresponding point O8 and the ninth corresponding point O9 to get a peak with the maximum value. The peak with the maximum value that falls at the position 0.05 seconds after the eighth corresponding point O8 is the feature point LCV.

After step S1048, the signals are recorded and stored as mentioned in the previous experiment.

Figure 30:
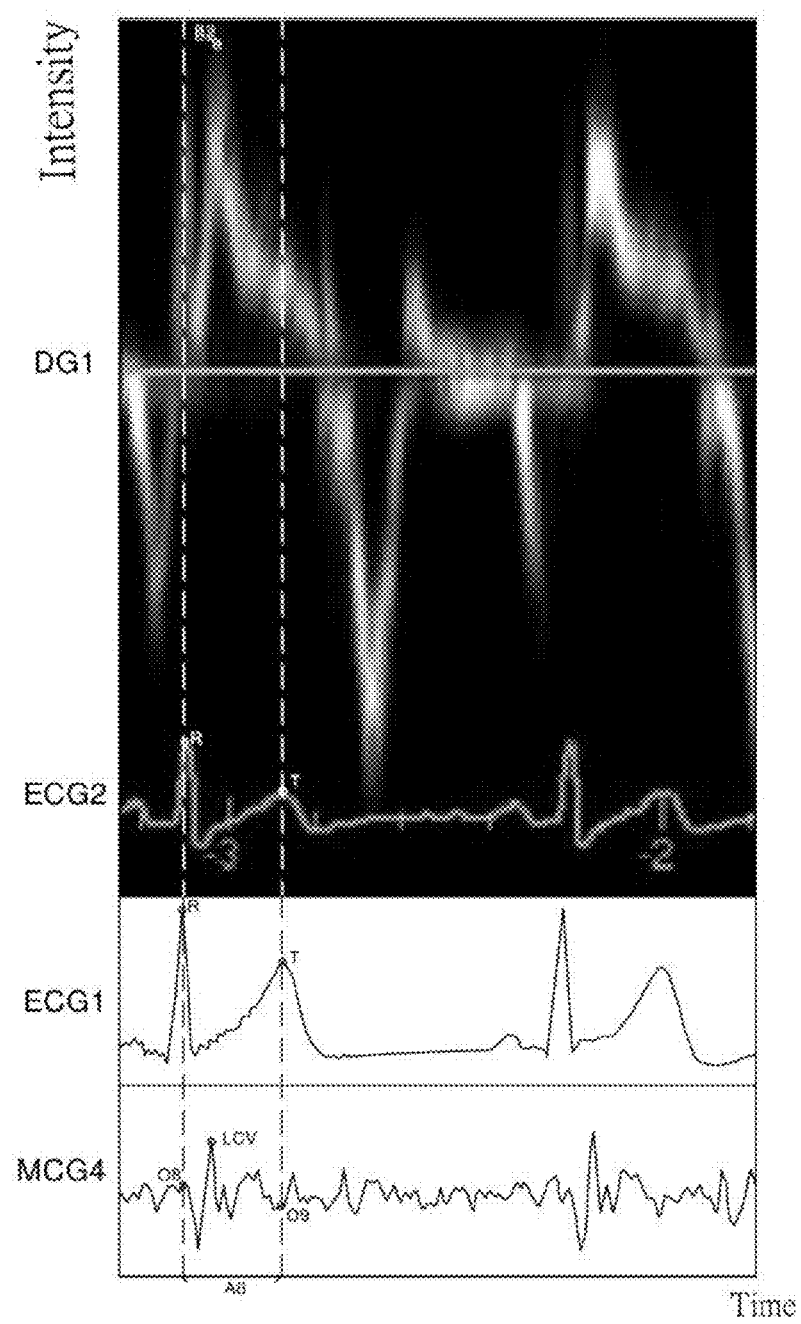
FIG. 30 is the seventh comparative figure showing signal strength versus time of the tenth set of observations according to the present invention.

Refer to FIG. 30. This figure depicts a comparative figure of the tenth experiment of the present invention. As shown in the figure, the horizontal axis and the vertical axis of the ECG1, the ECG2, the MCG4 and the DG1 in this figure are the same as those of the first comparative figure of the first experiment. Similar to the first and the second experiment, a Doppler ultrasonic device is used to detect heartbeat-induced vibrations on the body surface and obtain the DG1 for identification of the position of the feature point LCV of the MCG1 at the same time.

Refer to the DG1. There is a peak B2 with the maximum value showing maximum contraction velocity of the lateral wall at the left ventricle and being considered to be identical with the feature point LCV by physicians. This is in accordance to the peak B2 with the maximum value and several peaks and valleys in the eighth time interval A8 of the MCG4. Both the feature point LCV of the MCG4 and the peak B2 with the maximum value of the DG1 fall in the eighth time interval A8 while the B2 and the LCV are peaks with the maximum value within the eighth time interval A8. Thus the feature point LCV of the MCG4 and the peak B2 with the maximum value of the DG1 are identical to each other. In summary, the above experiments use at least one gravity sensor 11-14 to get the transmitral atrial contraction maximal flow feature point ($MF_A$), the lateral wall contraction maximal velocity feature point (LCV), the transaortic maximal flow feature point (AF), the trans-pulmonary maximal flow feature point (PF) and the septal wall contraction maximal velocity feature point (SCV). The MCG has the feature of multi-dimensional observation provided by at least one gravity sensor. Moreover, the feature point identification method for mechanocardiography of the present invention retrieves the feature point LCV and uses the LCV as the baseline, and then the feature point AF, the feature point PF and the feature point SCV are further retrieved. The gravity sensors 11-14 used in the present invention are lightweight and portable. Compared with ultrasonic devices used in medical institutes, the convenience in measurement is improved. Furthermore, several Doppler echocardiographs DG1~DG4 are obtained by using the Doppler ultrasonic device to detect heartbeat-induced vibrations on the body surface corresponding to heart valves. The results show that the gravity sensors 11~14 get the feature points ($MF_A$, LCV, AF, PF, and SCV) of the MCG corresponding to the same time sequences of the Doppler echocardiography. The above results are all assessed and confirmed by physicians.

In summary, the feature point identification method for mechanocardiography of the present invention uses gravity sensors disposed on heart valve auscultation sites including an aortic area, a mitral area, a pulmonary area and a tricuspid area to get feature points. The gravity sensors measure the vibrations on the body surface to get a first MCG, a second MCG, a third MCG, and a fourth MCG, which are compared with P-wave peak, R-wave peak and T-wave peak of at least one ECG measured by ECG sensing module to get corresponding points. Then several peaks and valleys within a certain time interval are retrieved to get readings related to heart valves, myocardial contraction and cardiac blood flow, including the transmitral atrial contraction maximal flow feature point ($MF_A$), the lateral wall contraction maximal velocity feature point (LCV), the transaortic maximal flow feature point (AF), the trans-pulmonary maximal flow feature point (PF) and the septal wall contraction maximal velocity feature point (SCV). In addition, at least one MCG is compared with the Doppler Echocardiography and physicians have checked and identified the above features related to heart valves, myocardial contraction and cardiac blood flow as consistent with the results of the Doppler Echocardiography. Therefore the present invention provides physicians with the signal strength or time parameter related to the feature points of the MCG for assessment of heart valvular diseases and physicians can combine the feature points of the MCG with data obtained by medical equipment so as to improve the accuracy of disease assessment.

Additional advantages and modifications will readily occur to those practicing this field and related fields. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A feature point identification method for mechanocardiography (MCG) applied to get a lateral wall contraction maximal velocity feature point (LCV) comprising the steps of:

placing a gravity sensor on a mitral area on a body surface corresponding to a patient's heart valves to get an MCG reading by the gravity sensor;

arranging an electrocardiography (ECG) sensing module at a limb lead attachment region on the body surface to get an ECG;

determining an R-wave peak and a T-wave peak of the ECG and corresponding the R-wave peak and the T-wave peak to the MCG reading, respectively, to get a first corresponding point and a second corresponding point of the MCG reading, respectively;

determining a peak with the maximum value in an interval from 0.04 seconds after the first corresponding point and the second corresponding point; wherein the peak with the maximum value is the lateral wall contraction maximal velocity feature point (LCV);

and using a processor for both of the determining steps.

2. The method as claimed in claim 1, wherein the mitral area is ranging from the right intercostal space at the right sternal border to the posterior axillary line.

3. The method as claimed in claim 1, wherein the limb lead attachment region includes one right arm (RA), one left arm (LA), and one left leg (LL).

* * * * *